United States Patent
Reddy et al.

(10) Patent No.: US 9,845,302 B2
(45) Date of Patent: Dec. 19, 2017

(54) ANTICANCER COMPOUNDS AND PROCESS FOR THE PREPARATION THEREOF

(71) Applicant: Council of Scientific and Industrial Research, New Delhi (IN)

(72) Inventors: Dumbala Srinivasa Reddy, Pune (IN); Kishor Laxman Handore, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 14/768,883

(22) PCT Filed: Feb. 19, 2014

(86) PCT No.: PCT/IN2014/000103
§ 371 (c)(1),
(2) Date: Aug. 19, 2015

(87) PCT Pub. No.: WO2014/128723
PCT Pub. Date: Aug. 28, 2014

(65) Prior Publication Data
US 2016/0002193 A1  Jan. 7, 2016

(30) Foreign Application Priority Data
Feb. 19, 2013 (IN) .......................... 0466/DEL/2013

(51) Int. Cl.
| | |
|---|---|
| C07D 307/94 | (2006.01) |
| C07D 493/10 | (2006.01) |
| C07D 301/00 | (2006.01) |
| C07C 67/347 | (2006.01) |
| C07C 45/61 | (2006.01) |
| C07C 45/27 | (2006.01) |
| C07C 45/67 | (2006.01) |
| A61K 31/34 | (2006.01) |
| A61K 31/343 | (2006.01) |

(52) U.S. Cl.
CPC ............ *C07D 307/94* (2013.01); *C07C 45/27* (2013.01); *C07C 45/61* (2013.01); *C07C 45/67* (2013.01); *C07C 67/347* (2013.01); *C07D 301/00* (2013.01); *C07D 493/10* (2013.01)

(58) Field of Classification Search
CPC .. C07D 307/94; C07D 493/10; C07D 301/00; C07C 45/67; C07C 45/27; C07C 67/347; C07C 45/61
See application file for complete search history.

(56) References Cited

U.S. PATENT DOCUMENTS 6,384,035 B1 * 5/2002 Hutchings ............ C07D 211/76
514/210.02

FOREIGN PATENT DOCUMENTS

WO    WO-2014/128723 A2    8/2014

OTHER PUBLICATIONS

Srikrishna, A. "Enantiospecific formal total synthesis of homogynolide-A", 2001 ARKIVOC (viii); 9-19.*
Srikrishna, A., "Enantiospecific synthesis of (+)-(1S, 2R, 6S)-1,2-dimethylbicyclo [4.3. 0] nonan-8-one and (−)-7-epibakkenolide-A." Tetrahedron 54.38 (1998): 11517-11524.*
Angeles, A. R., "Total synthesis of peribysin E necessitates revision of the assignment of its absolute configuration." Angewandte Chemie International Edition 46.9 (2007): 1451-1454.*
"International Application No. PCT/IN2014/000103, International Search Report dated Mar. 30, 2015", (dated Mar. 30, 2015), 5 pgs.
Angeles, Angie R., et al., "Total Synthesis of (+)- and (−)-Peribysin E", J. Am. Chem. Soc., 130(41), (2008), 13765-13770.
Handore, Kishor L., et al., "A Diverted Total Synthesis of Potent Cell Adhesion Inhibitor Peribysin E Analogues", Organic Letters, 15(8), (2013), 1894-1897.
Lee, Hung-Yi, et al., "Stereoselective Total Synthesis of (+−)-Peribysin E", J. Organic Chem., 77(1), (2012), 598-605.
Srikrishna, A., et al., "A radical cyclisation based cyclopentenone annulation of allyl alcohols", Tetrahedron Asymmetry, 14(19), (2003), 2975-2983.
Yamada, Takeshi, et al., "Absolute Stereostructures of Cell-adhesion Inhibitors, Peribysins A, E, F and G, Produced by a Sea Hare-derived *Periconia* sp.", J. Antibiot., 58(3), (2005), 185-191.
"International Application No. PCT/IN2014/000103, International Preliminary Report on Patentability dated Aug. 25, 2015", 10 pgs.
"International Application No. PCT/IN2014/000103, Written Opinion dated Mar. 30, 2015", 9 pgs.
Banerjee, Tanmay, et al, "Interfacial charge recombination of Os(II)-polypyridyle-resorcinol complex on oleic acid capped $TiO_2$ surface: what determines the dynamics?", *New J. Chem.*, 37, (2013), 3100-3108.
Banerjee, Tanmay, et al., "Newly Designed Resorcinolate Binding for Ru(II)- and Re(I)-Polypyridyl Complexes on Oleic Acid Capped $TiO_2$ in Nonaqueous Solvent: Prolonged Charge Separation and Substantial Thermalized MLCT Injection", *J. Phys. Chem. C.* 117, (2013), 3084-3092.

(Continued)

*Primary Examiner* — Matt Mauro
(74) *Attorney, Agent, or Firm* — Schwegman Lundberg & Woessner, P.A.

(57) ABSTRACT

The invention disclosed herein relates to novel Peribysin E analogs of general formula-I. Further the invention provides simple, economical and short synthesis of Peribysin E and its analogs of Formula I, in good yield and purity leading to the identification of more potent cell adhesion inhibitors.

General formula-I

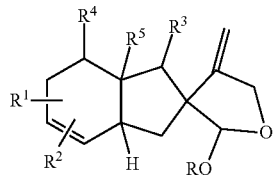

10 Claims, 4 Drawing Sheets

(56) References Cited

OTHER PUBLICATIONS

Banerjee, Tanmay, et al., "Synthesis, Steady-State, and Femtosecond Transient Absorption Studies of Resorcinol Bound Ruthenium(II)- and Osmium(II)-polypyridyl Complexes on Nano-TiO$_2$ Surface in Water—", *Inorg. Chem.,* 52, (2013), 5366-5377.

Debnath, Tushar, et al., "Ultrafast Electron Injection, Hole Transfer, and Charge Recombination Dynamics in CdSe QD Super-Sensitized Re(I)-Polypyridyl Complexes with Catechol and Resorcinol Moiety: Effect of Coupling", *J. Phys. Chem. C,* 119, (2015), 3522-3529.

Kaniyankandy, Sreejith, et al., "Does Bridging Geometry Influence Interfacial Electron Transfer Dynamics? Case of the Enediol-TiO$_2$ System", *J. Phys. Chem. C,* 116, (2012), 98-103.

\* cited by examiner

ANTICANCER COMPOUNDS AND PROCESS FOR THE PREPARATION THEREOF

PRIORITY CLAIM TO RELATED APPLICATIONS

This application is a U.S. national stage application filed under 35 U.S.C. §371 from International Application Serial No. PCT/IN2014/000103, which was filed 19 Feb. 2014, and published as WO2014/128723 on 28 Aug. 2014, and which claims priority to Indian Application No. 0466/DEL/2013, filed 19 Feb. 2013, which applications and publication are incorporated by reference as if reproduced herein and made a part hereof in their entirety, and the benefit of priority of each of which is claimed herein.

FIELD OF THE INVENTION

The present invention relates to compound of general formula 1 useful for the treatment of cancer. Particularly, present invention further relates to the simple, economical and short synthesis of Peribysin E and its analogues of general formula I, in good yield and purity leading to the identification of more potent cell adhesion inhibitors, which in turn can lead to the much needed anticancer agents for further development.

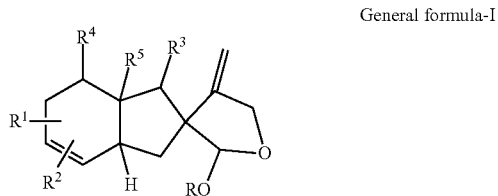

General formula-I

BACKGROUND OF THE INVENTION

A group of natural products called peribysins (A-G) were isolated by Yamada's group from a strain of *Periconia byssoides* OUPS-N133 originally separated from the sea hare, *Aplysia kurodai* (*Antibiot.* 2005, 58, 185). The structurally interesting natural products, especially peribysin E (1), attracted researcher attention toward developing anticancer and anti-inflammatory agents owing to its potent cell adhesion inhibitory activity. It was observed that the natural product (−)-peribysin E has shown more potent activity than the gold standard herbimycin (2) in the cell adhesion inhibition assay.

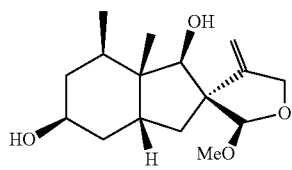

Peribysin E, 1
(cell adhesion
$IC_{50} = 11.5$ μM)

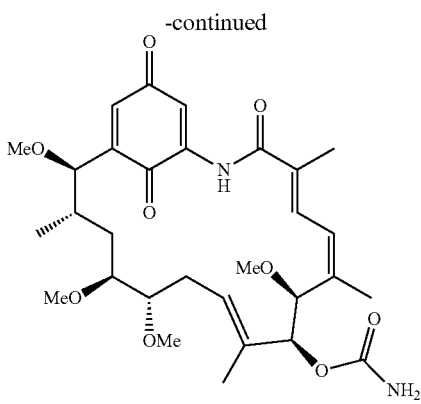

Herbimycin, 2
(cell adhesion
$IC_{50} = 38.0$ μM)

The treatment of Cancer, a broad group of more than 200 various diseases, all involving unregulated cell growth has become a major area of focus these days. When Cancer begins it invariably produces no symptoms with signs and thus the complicacy in its treatment is very high. In 2007, cancer caused about 13% of all human deaths worldwide (7.9 million).

Leukemia is a type of cancer of the blood or bone marrow characterized by an abnormal increase of immature white blood cells called "blasts." The HL-60 (Human promyelocytic leukemia cells) cell line is a leukemic cell line that has been used for study on how certain kinds of blood cells are formed. Further, inhibiting the adhesion of such Human-leukemia HL-60 cells to human-umbilical-vein endothelial cells (HUVEC) more potently has been continuously done but only some of the results have been successfully reported. A potent cell adhesion inhibitor was the main target for the treatment of such human leukemia.

In an Article titled "*Absolute Stereostructures of Cell-adhesion Inhibitors, Peribysins A, E, F and G, Produced by a Sea Hare-derived Periconiasp.*" by Takeshi Yamada, Mitsunobu Doi, Atsuko Miura, Waka Harada, Mika Hiramura, Katsuhiko Minoura, Reiko Tanaka, Atsushi Numatain *J. Antibiot.* 2005, 58, 185-191, relates to the first isolation of Peribysin E and related metabolites from a strain of *Periconia byssoides* OUPS-N133 originally separated from the sea hare, *Aplysia kurodai*. These natural products, especially peribysin E, were reported to inhibit adhesion of leukemia HL-60 cells to human-umbilical-vein endothelial cells (HUVEC). Because of its potent cell-adhesion inhibitory activity and its scarcity, peribysin E has become a target for total synthesis.

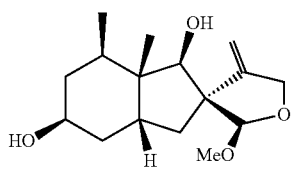

Peribysin E

An article titled "*Total Syntheses of (+)- and (−)-Peribysin E*" by Angie R. Angeles, Stephen P. Waters, and Samuel J. Danishefskyin *J. Am. Chem. Soc.* 2008, 130, 13765-13770, achieved the first total synthesis of both enantiomers of peribysin E and thereby reassigned the absolute configuration. In their elegant synthesis, a Diels-Alder reaction followed by semipinacol-type ring contraction served to secure the stereochemistry of peribysin E.

Danishefsky et al.

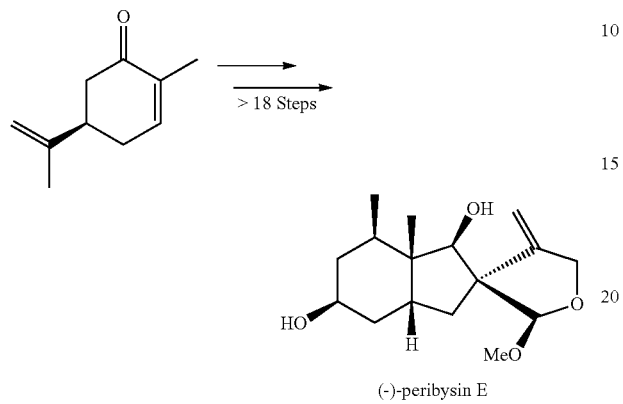

(−)-peribysin E

Further, recently published article titled "*Stereoselective Total Synthesis of (±)-Peribysin E*" by Hung-Yi Lee and Chin-Kang Shain (*J. Org. Chem.* 2012, 77, 598-605) reported a stereoselective total synthesis of (±)-peribysin E via α-carbonyl radical cyclization and semipinacol-type rearrangement. Their synthesis provided (±)-peribysin E in 3.2% overall yield from 2-methylcyclohexen-1-one and is adaptable for preparation of analogues and derivatives of peribysin E for anticancer study.

Sha et al.

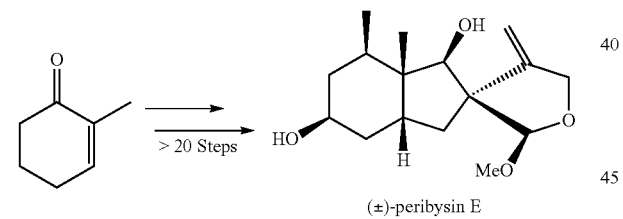

(±)-peribysin E

Accordingly, the discovery and development of new cell adhesion inhibiting agents and their total synthesis therefore remains the need of the hour.

The prior art processes as described above for the synthesis of Peribysin E suffer from several drawbacks including being very long and strenuous routes for synthesis of the compound and involves the use of costly reagents which makes the process uneconomical. Further, the routes of synthesis for Peribysin E and compounds thereof included in the prior art leads to poor yields and thus the problem of scarcity still persists.

OBJECTIVE OF THE INVENTION

The main objective of the present invention is to provide a simple and economical route for synthesis of a class of compounds belonging to Peribysin E, having cell adhesion inhibiting property.

Another object of the present invention is to provide the process for the preparation of compounds which directly lead to the formation of pure isomer of the desired compound.

SUMMARY OF THE INVENTION

Accordingly, present invention provides a compound of general formula I

Formula-I

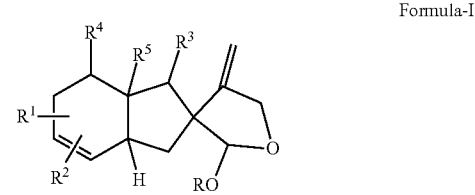

Wherein;

R is hydrogen or (C1-C8) alkyl, $R^1$, $R^2$, and $R^3$ each are individually selected from the group consisting of H, OH, OR or $R^1$ and $R^2$ together may form 4-8 membered alicyclic, aromatic ring which may additionally contain an hetero atom, or $R^1$ and $R^2$ together form epoxide ring;

$R^4$ and $R^5$ are selected from hydrogen, C1-C8 alkyl, $CONR^2$, COOR; or $R^4$ and $R^5$ may form 4-8 membered alicyclic ring which may additionally contain heteroatom.

In an embodiment of the present invention, said compound exhibit cell adhesion inhibition activity wherein the inhibition concentration at 50% ($IC_{50}$) is in the range of 2.0-20.0 µM.

In yet another embodiment of the present invention, representative compounds comprising:

i) (2R,2'R,3'R,3a'S,4'R,7a'R)-2-methoxy-3a',4'-dimethyl-4-methylene 1',3',3a',4,4',5,5',7a'-octahydro-2H-spiro[furan-3,2'-inden]-3'-ol (9);

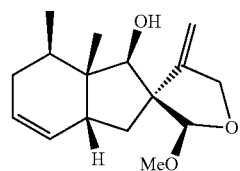

ii) (1a'R,2R,3R,3'R,3a'S,4'R,6a'S,6b'S)-2-methoxy-3',3a'-dimethyl-4-methylenedecahydro-2H-spiro[furan-3,5'-indeno[4,5-b]oxiren]-4'-ol (10);

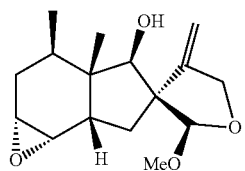

iii) (1'R,2R,2'R,3a'R,5'R,7'R,7a'S)-2-methoxy-7',7a'-dimethyl-4-methylene decahydro-2H-spiro[furan-3,2'-indene]-1',5'-diol (11a);

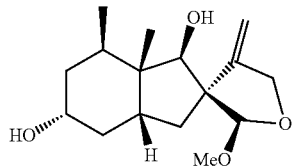

iv) (1'R,2R,2'R,3a'S,4'R,7'R,7a'S)-2-methoxy-7',7a'-dimethyl-4-methylenedecahydro-2H-spiro[furan-3,2'-indene]-1',4'-diol (11b);

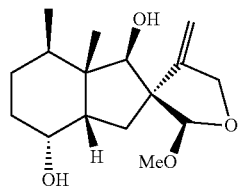

v) (1'R,2R,2'R,3a'S,4'S,7'R,7a'S)-2-methoxy-7',7a'-dimethyl-4-methylenedecahydro-2H-spiro[furan-3,2'-indene]-1',4'-diol (11c);

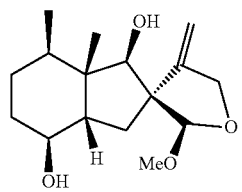

vi) (1'R,2R,2'R,3a'S,7'R,7a'S)-2-methoxy-7',7a'-dimethyl-4-methylene decahydro-2H-spiro[furan-3,2'-inden]-1'-ol (20);

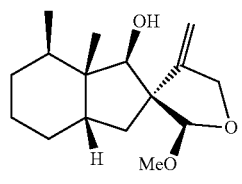

vii) (1'R,2R,2'R,3a'S,7'R,7a'S)-2-methoxy-7',7a'-dimethyl-4-methylene decahydro-2H-spiro[furan-3,2'-indene]-1',4',5'-triol (21);

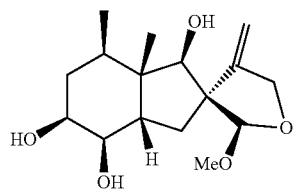

viii) (1'R,2R,3R,3a'S,4'S,5'R,7'R,7a'S)-2-methoxy-7',7a'-dimethyl-4-methylenedecahydro-2H-spiro[furan-3,2'-indene]-1',4',5'-triol (22).

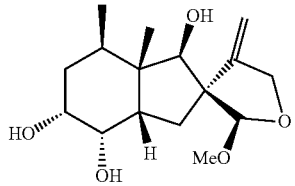

In yet another embodiment, present invention provides a process for the preparation of compound of general formula-I wherein the process comprises the steps of:

a) reacting compound of formula-II with compound of formula-III in the ratio ranging between 1 to 2.5 in presence of $BF_3.Et_2O$ in suitable organic solvent at lower temperature in the range of (−)78 to 25° C. to obtain compound of formula-IV;

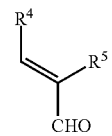

Formula-II

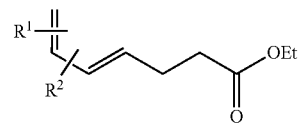

Formula-III

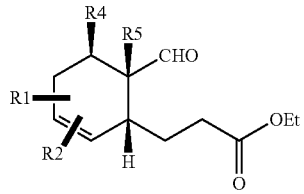

Formula-IV b) reducing compound of formula IV with lithium aluminum hydride (LAH) in the ratio ranging between 1 to 4 in presence of organic solvent to obtain diol compound (4) followed by oxidizing in presence of Collins reagent to obtain corresponding aldehyde (5);

c) subjecting compound (5) to intramolecular aldol reaction in presence of aqueous alkali metal hydroxide and lower alcohol to obtain intermediate compound (6);

d) oxidizing compound (6) under Wacker conditions to obtain highly regioselective keto-aldehyde (12) followed by selective reduction at lower temperature in the range of −80° C. to 0° C. to obtain alcohol (13);

e) subjecting compound (13) to reduction in presence of lithium amide to obtain alcohol (14), followed by oxidizing to obtain α,β-unsaturated aldehyde (15) using $MnO_2$; subsequently epoxidising compound (15) to obtain corresponding epoxide (16), which further treated with iodoalcohol to obtain diastereomeric mixture of compound (17); and f) treating compound (17) with 2,6-lutidine and TMSOTf followed by reacting with methanolic HCl to obtain crude Peribysin E (1), optionally purifying the crude Peribysin E by the known process to obtain Peribysin-E of formula 1;

g) epoxidising intermediate compound (6) as obtained in step (c), to obtain oxirene-carbaldehyde compound (7) followed by reacting with iodoalcohol to obtain diastereomeric mixture of compound (8);

h) treating compound (8) with 2,6-lutidine and TMSOTf followed by reacting with methanolic HCl to obtain crude compound (9);

i) epoxidising compound (9) in presence of mCPBA to obtain compound (10);

j) reducing oxirane compound (10) in presence of lithium aluminum hydride, to obtain three stereoisomers (11a), (11b) and (11c);

k) hydrogenating oxirene-carbaldehyde intermediate (7) as obtained in step (g), to obtain saturated hydrindane (18);

l) reacting compound (18) with iodoalcohol, to obtain diastereomeric mixture of compound (19);

m) treating compound (19) with 2,6-lutidine and TMSOTf, followed by reacting with methanolic HCl, to obtain desired analogue of Peribysin E of formula-I, compound (20).

n) subjecting compound 9 as obtained in step (h) to dihydroxylation in presence of $OsO_4$-catalyst to furnish mixture of triols 21 and 22 in a highly chemoselective.

In yet another embodiment of the present invention, the alkali metal hydroxide used is selected from the group consisting of KOH, NaOH, $Ca(OH)_2$ or mixtures thereof.

In yet another embodiment of the present invention, wherein selective reduction is carried out in presence of $NaBH_4$, $LiBH_4$, $Zn(BH_4)_2$ or $AlH_3$.

In yet another embodiment of the present invention, the organic solvent used is selected from the group consisting of THF, DCM, Acetonitrile, DMF, Ethyl acetate, DMSO or mixtures thereof.

In yet another embodiment, present invention provides a pharmaceutical composition comprising compound of general formula I, and stereoisomers and pharmaceutically acceptable salts thereof, together with pharmaceutically acceptable excipients and/or vehicles, for inhibiting cellular adhesion.

In yet another embodiment, present invention provides a method of treating or inhibiting cellular adhesion in a subject comprising administrating compound of general formula I, optionally along with pharmaceutically acceptable excipients and/or vehicles, wherein the subject is human.

In yet another embodiment, present invention provides use of compound of the general formula I for the preparation of medicament useful for treating or inhibiting the cell adhesion in a subject, wherein the subject is human.

DETAILED DESCRIPTION OF THE INVENTION

The present invention provides analogues of Peribysin E of the general formula I

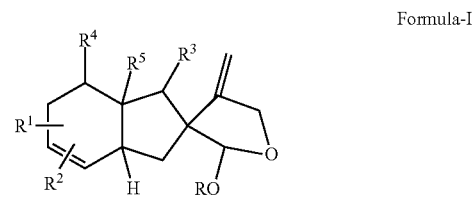

Formula-I wherein
R is hydrogen or (C1-C8) alkyl,
$R^1$, $R^2$, and $R^3$ each are individually selected from the group consisting of H, OH, OR or $R^1$ and $R^2$ together may form 4-8 membered alicyclic, aromatic ring which may additionally contain an hetero atom, or $R^1$ and $R^2$ together form epoxide ring;
$R^4$ and $R^5$ are selected from the group consisting of hydrogen, (C1-C8) alkyl, $CONR^2$, COOR; or $R^4$ and $R^5$ may form 4-8 membered alicyclic ring which may additionally contain heteroatom.

The present invention discloses a simple, economical and short process for the preparation of a class of compounds belonging to Peribysin E of general formula I, stereoisomers and pharmaceutically acceptable salts thereof exhibiting cell adhesion inhibiting property, in good yield and purity.

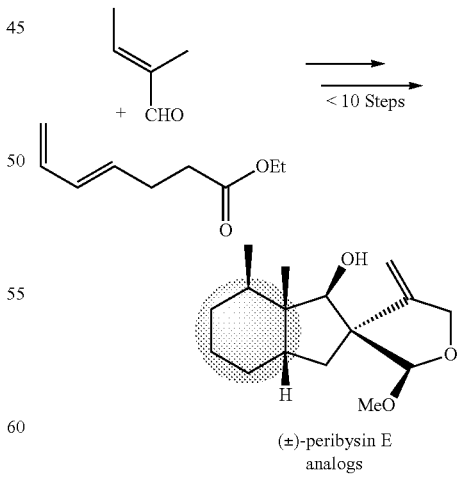

(±)-peribysin E analogs

The process encompasses diastereomers due to presence of chiral groups along with its structural analogues.

Figure 1A:
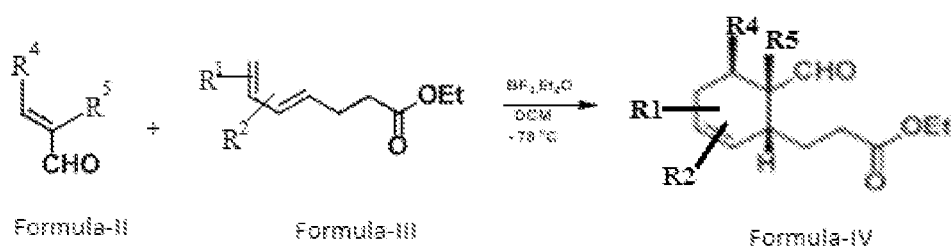
FIG. 1A: Reaction of compound of Formula-II with compound of Formula-III in the presence of $BF_3.Et_2O$ in organic solvent at low temperature to obtain compound of Formula-IV.

According to the invention, the process encompasses the step of reaction of compound of Formula-II with compound of Formula-III in presence of BF$_3$.Et$_2$O in organic solvent at lower temperature to obtain compound of Formula-IV as shown in FIG. 1A, wherein R$^1$ and R$^2$ each individually selected from the group consisting of H, OH, OR; where R is hydrogen or (C1-C8) alkyl or R$^1$ and R$^2$ may from 4-8 membered alicyclic, aromatic ring which may additionally contain heteroatom, or R$^1$ and R$^2$ together form epoxide ring; R$^4$ and R$^5$ are selected from hydrogen, C1-C8 alkyl, CONR$^2$, COOR or R$^4$ and R$^5$ may form 4-8 membered alicyclic ring which may additionally contain heteroatom.

The compounds of formula-II is selected from the group consisting of (2E)-2-methylbut-2-enal (1), prop-2-enal; the compound of formula-III is particularly ethyl (4E)-hepta-4, 6-dienoate (2), and the compound of formula-IV is selected from the group consisting of ethyl 3-((1R,5R,6S)-6-formyl-5,6-dimethylcyclohex-2-en-1-yl) propanoate (3); ethyl 3-[(1R,6S)-6-formylcyclohex-2-en-1-yl]propanoate.

The compound of formula-III on subsequent process steps yields Peribysin E and novel analogues thereof having formula I with high yield.

Figure 1B:
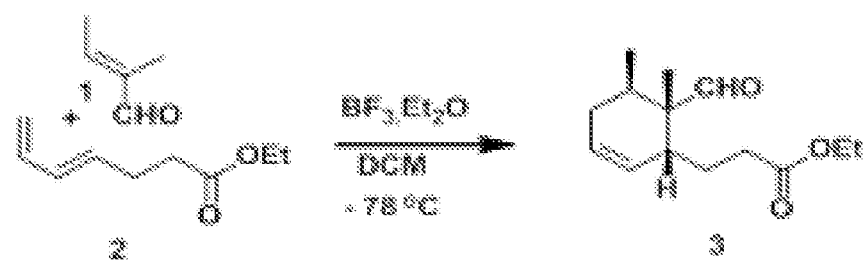
FIG. 1B: The short process for the preparation of Peribysin E and analogues of formula I commences with the reaction of (2E)-2-methylbut-2-enal (1) with ethyl (4E)-hepta-4, 6-dienoate (2) in presence of $BF_3.Et_2O$ in organic solvent at lower temperature, to obtain ethyl 3-((1R,5R,6S)-6-formyl-5,6-dimethylcyclohex-2-en-1-yl) propanoate (3).

The short process for the preparation of Peribysin E and analogues of formula I, commence with the reaction of (2E)-2-methylbut-2-enal (1) with ethyl (4E)-hepta-4, 6-dienoate (2) in presence of BF$_3$.Et$_2$O in organic solvent at lower temperature, to obtain ethyl 3-((1R,5R,6S)-6-formyl-5,6-dimethylcyclohex-2-en-1-yl) propanoate (3), as depicted in FIG. 1B.

Figure 2:
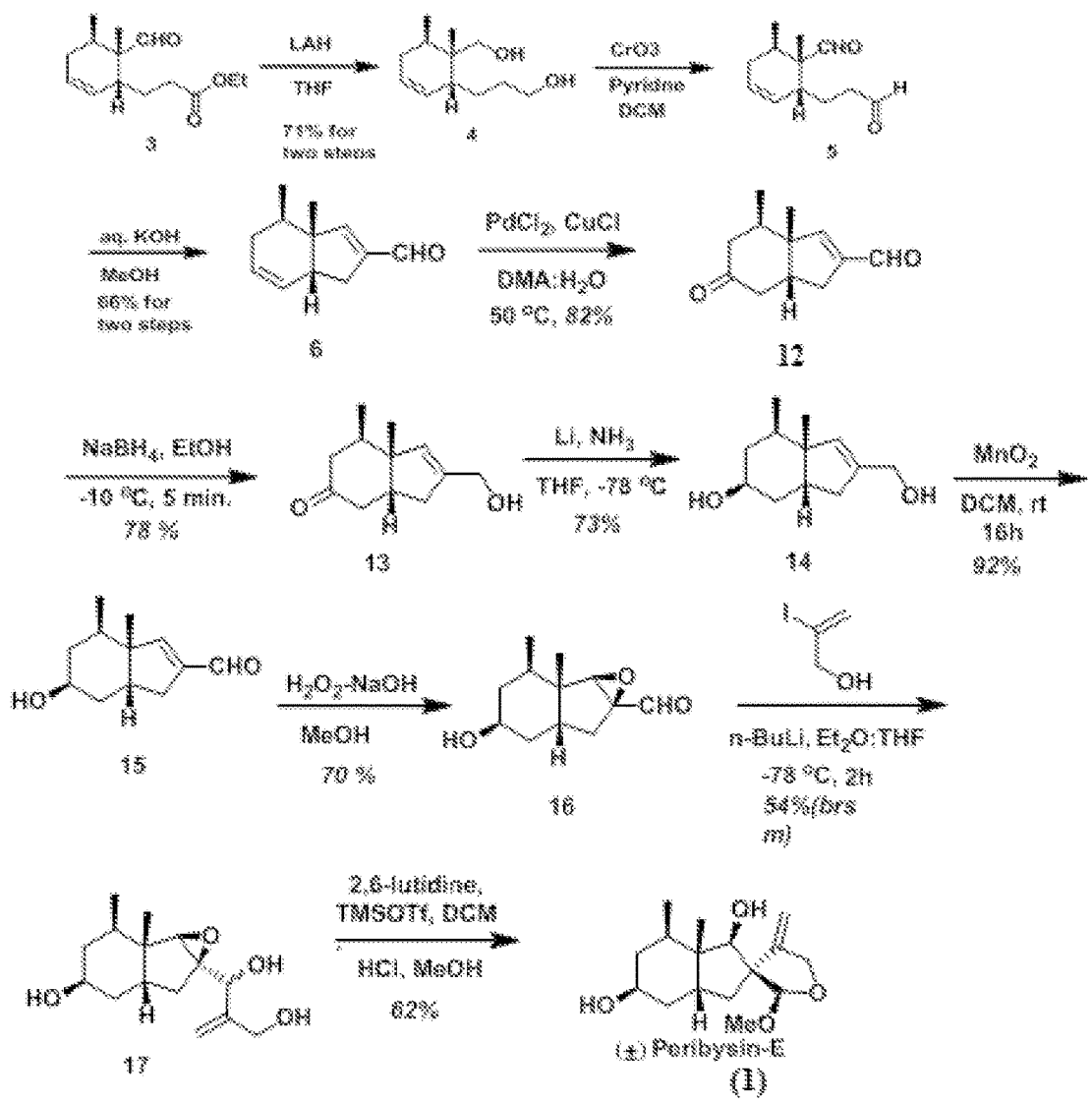
FIG. 2: Synthesis of (±) Peribysin E (1).

The invention provides cost effective, short process for the synthesis of (±) Peribysin E (1), represented as in FIG. 2.

The said process comprises the steps of
a) reducing compound (3) with lithium aluminum hydride in presence of organic solvent to obtain diol compound (4); followed by oxidizing compound (4) in presence of Collins reagent to obtain corresponding aldehyde (5);
b) subjecting compound (5) to intramolecular aldol reaction in presence of aqueous alkali metal hydroxide and lower alcohol to obtain intermediate compound (6);
c) oxidizing compound (6) under Wacker conditions to obtain highly regioselective keto-aldehyde (12), which on selective reduction at lower temperature, furnishes alcohol (13);
d) subjecting compound (13) to reduction in presence of lithium amide to obtain alcohol (14), followed by oxidizing of alcohol to obtain α,β-unsaturated aldehyde (15) using MnO$_2$;
e) subsequently, epoxidising compound (15) to obtain corresponding epoxide (16), which further treated with iodoalcohol to obtain diastereomeric mixture of compound (17);
f) treating compound (17) with 2,6-lutidine and TMSOTf followed by reacting with methanolic HCl to obtain crude Peribysin E, optionally purifying the crude Peribysin E (1) by known process.

Figure 3:
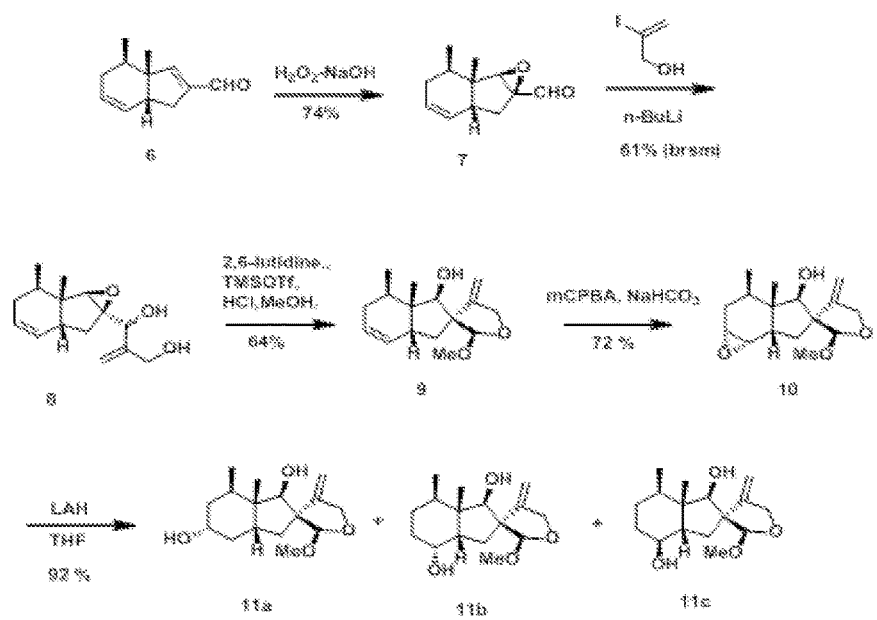
FIG. 3: Synthesis of a class of compounds belonging to Peribysin E of the general formula I, namely (9), (10), (11a), (11b) and (11c) from intermediate compound (6).

The present invention provides a synthesis for the preparation of class of compounds belonging to Peribysin E of the general formula I, namely (9), (10), (11a), (11b) and (11c) from intermediate compound (6) as depicted in FIG. 3 comprising the steps of:
a) epoxidising intermediate compound (6), to obtain oxirene-carbaldehyde compound (7); followed by reacting with iodoalcohol to obtain diastereomeric mixture of compound (8);
b) treating compound (8) with 2,6-lutidine and TMSOTf followed by reacting with methanolic HCl to obtain crude Peribysin E analogue of Formula-I (9);
c) epoxidising compound (9) in presence of mCPBA to obtain Peribysin E analogue of Formula-I (10); and
d) reducing oxirane compound (10) in presence of lithium aluminum hydride, to obtain three stereoisomers of Peribysin E analogues of Formula-I, namely (11a), (11b) and (11c).

Further the purification and isolation of the isomer obtained by the instant process may optionally be carried out by MPLC (combiflash rf) column chromatography.

According to the process the organic solvent is selected from the group consisting of THF, DCM, Acetonitrile, DMF, Ethyl acetate, DMSO or mixtures thereof.

The alkali metal hydroxide is selected from KOH, NaOH, Ca(OH)$_2$ or mixtures thereof. Further selective reduction is carried out in presence of NaBH$_4$, Zn(BH$_4$)$_2$, AlH$_3$ at lower temperature ranging from −80° C. to 0° C., preferably −78° to −10° C.

The epoxidation of intermediate compound 6 takes place in presence of 10-40% aqueous H$_2$O$_2$ and in presence of 5-10 N NaOH at 0° C.

The alcohol employed in the process is preferably lower alcohol selected from the group consisting of methanol, ethanol, propanol, butanol, isopropanol, tert-butanol and mixture thereof.

'Collins reagent' is the complex of chromium(VI) oxide with pyridine in dichloromethane (*Tetrahedron Lett.* 9 (30): 3363-3366) used to selectively oxidize primary alcohols to the aldehyde.

The 'Wacker process' is carried out in presence of palladium(II) chloride and copper(I) chloride in a water/dimethylformamide or dimethylacetamide solvent mixture in the presence of oxygen (*Org. Synth.* 1984, 62, 9).

Figure 4:
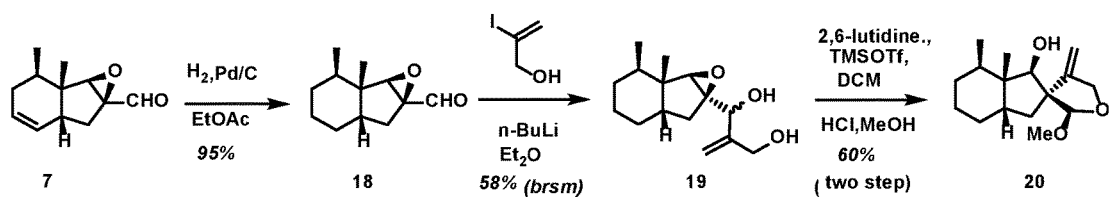
FIG. 4: Synthesis of some analogues of peribysin E of formula-I, e.g., compount (20), from oxirene-carbaldehyde intermediate (7).

The invention provides process for the preparation of desired analogues, of peribysin E of formula-I i.e. compound (20), from oxirene-carbaldehyde intermediate (7), (as depicted in FIG. 4) comprises steps of:
a) hydrogenating oxirene-carbaldehyde intermediate (7) to obtain saturated hydrindane (18);
b) reacting compound (18) with iodoalcohol to obtain diastereomeric mixture of compound (19);
c) treating compound (19) with 2,6-lutidine and TMSOTf, followed by reacting with HCl/MeOH to obtain desired analogue of Peribysin E of Formula-I, compound (20).

Figure 5:
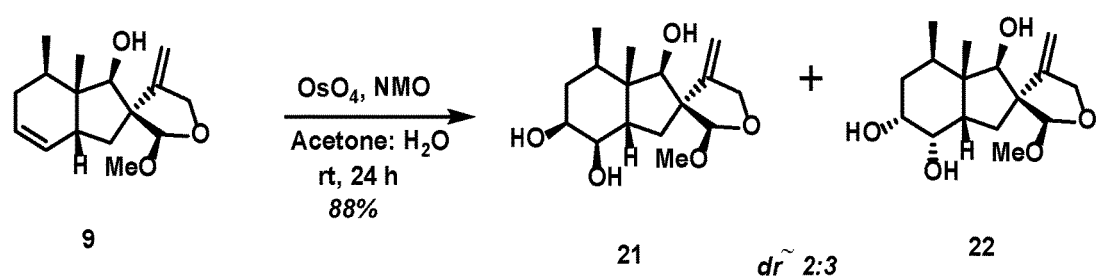
FIG. 5: Synthesis of a mixture of triol analogues of peribysin E of formula-I, namely (21) and (22), from peribysin analogue compound (9). The process includes subjecting compound 9 to dihydroxylation in presence of $OsO_4$-catalyst to furnish a mixture of triols 21 and 22 in a highly chemoselective manner.

In yet another embodiment, the invention provides process for the preparation of mixture of triol analogues of peribysin E of formula-I, namely (21) and (22), from peribysin analogue compound (9), wherein the process comprises, subjecting compound 9 to dihydroxylation in presence of OsO$_4$-catalyst to furnish a mixture of triols 21 and 22 in a highly chemoselective manner (as depicted in FIG. 5).

In another embodiment, the invention provides, the synthesized novel peribysin E analogues of Formula-I exhibit cell adhesion inhibition property. Further the synthesized compounds of Formula-I analyzed for HL60-HUVEC Cell adhesion inhibition activity, wherein IC$_{50}$ value thus obtained is in the range of 2.0 to 20.0 μM.

The novel analogues of peribysin E of Formula-I may be indicated for other therapeutic conditions including, but not restricted to anti-cancer agent, anti-tumour agents, anti-inflammatory agents, anti-bacterial agents and such like.

The invention provides a pharmaceutical composition comprising a compound of formula (I), or a stereoisomer, or ester or pharmaceutically acceptable salt thereof, along with pharmaceutically acceptable carrier, diluent or excipient.

The compound of formula (I) disclosed herein is present in the composition in an amount which is effective to treat the disease or the condition caused by the bacterial strains.

The pharmaceutical compositions of the invention can be prepared by combining a compound of the invention with appropriate pharmaceutically acceptable carriers, diluents or excipients or vehicles and may be formulated into preparations in solid, semi-solid, liquid or gaseous forms, such as tablets, capsules, powders, granules, ointments, solutions, injections, gels and microspheres.

The present invention relates to administering 'an effective amount' of the 'composition of invention' to the subject suffering from diseases such as bacterial infections, tumors, cancer, inflammation. Accordingly, the pharmaceutical compositions containing compound of formula I may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

Pharmaceutical compositions of the invention are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

Consequently, the present invention provides the synthesis of (±)-peribysin E in the shortest route. Further invention provides synthesis of the novel analogues (9) (10) (11a) (11b) (11c) (20) (21) (22) of peribysin E using diverted total synthesis toward identifying potent cell adhesion inhibitors.

EXAMPLES

Following examples are given by way of illustration therefore should not be construed to limit the scope of the invention.

Example 1

Synthesis of Ethyl 3-((1R,5R,6S)-6-formyl-5,6-dimethylcyclohex-2-en-1-yl) Propanoate (3)

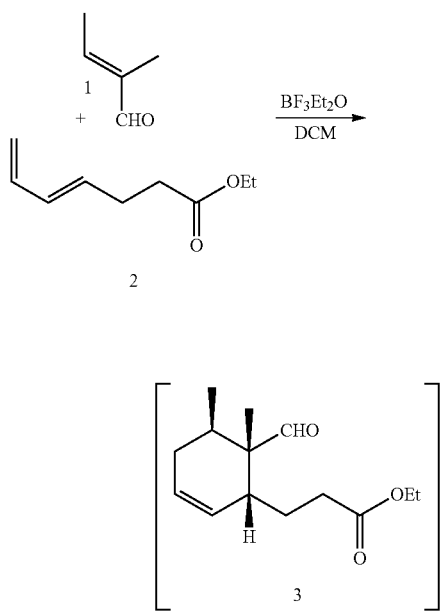

To a solution of diene (2) (6.0 g, 38.9 mmol) and (E)-2-methylbut-2-enal (1) (8.13 g, 96.7 mmol) in dry $CH_2Cl_2$ (200 mL) was added $BF_3.OEt_2$ (10.9 g, 77.4 mol) dropwise at −78° C. The mixture was allowed to warm to room temperature (25° C.) and was stirred for 6 h at room temperature (25° C.). The $CH_2Cl_2$ layer was washed with 10% $NaHCO_3$ (3×100 mL) followed by $H_2O$ (100 mL) and brine (100 mL), dried over $Na_2SO_4$, filtered and concentrated in vacuo. The crude material (3) obtained after removal of solvent directly used for next step without further purification.

Example 2

Synthesis of 3-((1R,5R,6S)-6-(Hydroxymethyl)-5,6-dimethylcyclohex-2-en-1-yl) propan-1-ol (4)

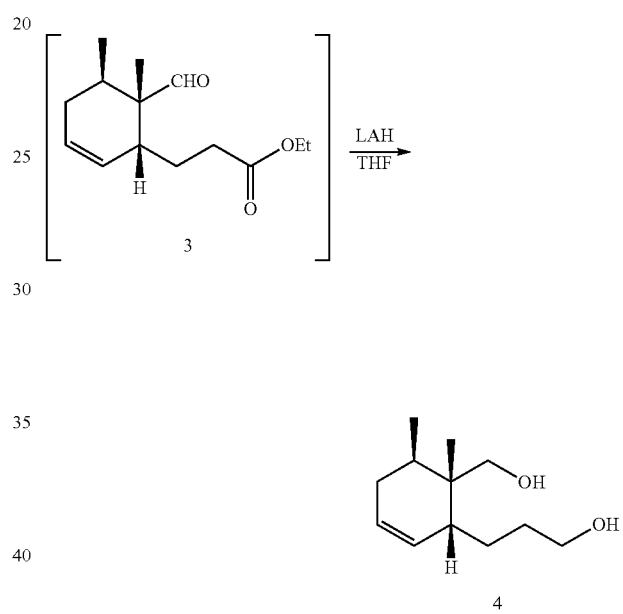

Crude 3 in dry THF (50 mL) was added dropwise to suspension of lithium aluminum hydride (3.64 g, 95.7 mmol) in dry THF (40 mL) at 0° C. and stirred for 2 h at room temperature (25° C.). After completion of starting material, saturated $Na_2SO_4$ (25 mL) and Ethyl acetate (50 mL) was carefully added. The resulting suspension was filtered through a pad of Celite and the solvent was removed in vacuo. The crude material obtained after removal of solvent was purified by column chromatography (silica gel 100-200, 4:6 ethyl acetate:pet.ether) to afford 4 (5.4 g, 71%) as a white solid.

Mp: 105-108° C.

IR$\upsilon_{max}$ (film): 3339, 3019, 2930, 1654, 1451, 1031 $cm^{-1}$.

$^1$H NMR (400 MHz, $CDCl_3$) δ 5.72-5.69 (m, 1H), 5.59-5.56 (m, 1H), 3.73-3.60 (m, 2H) 3.54-3.52 (m, 2H), 2.56 (bs, 1H), 2.37 (bs, 2H), 2.06-2.00 (m, 1H), 1.89-1.86 (m, 1H), 1.78-1.67 (m, 3H), 1.56-1.46 (m, 1H), 1.21-1.13 (m, 1H), 0.88 (s, 3H), 0.78 (d, J=6.6 Hz, 3H).

$^{13}$C NMR (100 MHz, $CDCl_3$) δ 129.5, 125.1, 67.9, 62.2, 40.6, 38.8, 31.8, 30.0, 29.7, 26.6, 16.8, 15.0.

HRMS (ESI) calc for $C_{12}H_{22}O_2Na^+$ 221.1510, found 221.1512.

Example 3

Synthesis of (3aS,4R,7aR)-3a,4-Dimethyl-3a,4,5,7a-tetrahydro-1H-indene-2-carbaldehyde (6)

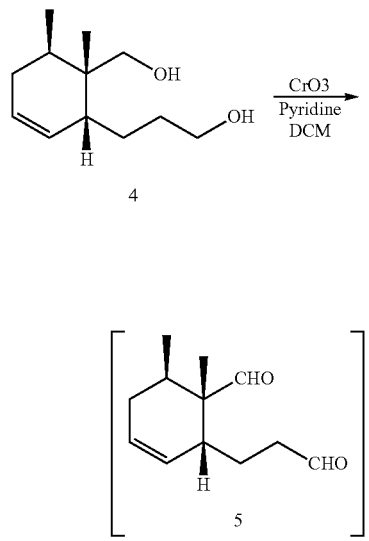

To a solution of pyridine (32.8 mL, 407.5 mmol) in dry DCM (150 mL) was added CrO₃ (20.3 g, 203 mmol). The mixture was stirred for 30 min at room temperature (23° C.). Then 4 (3.3 g, 16.6 mmol) in dry DCM (100 mL) was added. After 2 h diethyl ether was added and the mixture filtered. The organic layer was washed with 2M aqueous HCl, and 6% aqueous solution of NaHCO₃, water and brine, dried over Na₂SO₄, filtered and concentrated in vacuo. Crude compound 5 was dissolved in methanol (30 mL), cooled to 0° C., and added 15% KOH (20 mL). After stirring for 1 h, diluted with 100 mL of petroleum ether, washed with water, 1N HCl and brine. Flash chromatography (elution with EtOAc:hexanes; 1:9) afforded 6 (1.9 g, 66%) as light yellow oil.

IR$\upsilon_{max}$ (film): 3343, 3019, 2919, 2960, 2708, 1681, 1616, 1454, 1370 cm$^{-1}$.

$^1$H NMR (400 MHz, CDCl₃) δ 9.72 (s, 1H), 6.76 (s, 1H), 5.66-5.63 (m, 1H), 5.42-5.39 (m, 1H), 2.82-2.75 (m, 1H), 2.57-2.54 (m, 1H, 2.32-2.28 (d, J=15.98 Hz, 1H, 1.98-1.94 (m, 1H), 1.76-1.68 (m, 2H), 1.13 (s, 3H), 1.06 (d, J=6.7 Hz, 3H).

$^{13}$C NMR (100 MHz, CDCl₃) δ 190.3, 156.8, 145.9, 130.8, 126.0, 52.0, 45.7, 35.2, 33.7, 31.2, 23.8, 15.6.

HRMS (ESI) calc for C₁₂H₁₇O [M+H]⁺ 177.1225, found 177.1274.

Example 4

Synthesis of (3aS,4R,7aR)-3a,4-dimethyl-6-oxo-3a,4,5,6,7,7a-hexahydro-1H-indene-2-carbaldehyde (12)

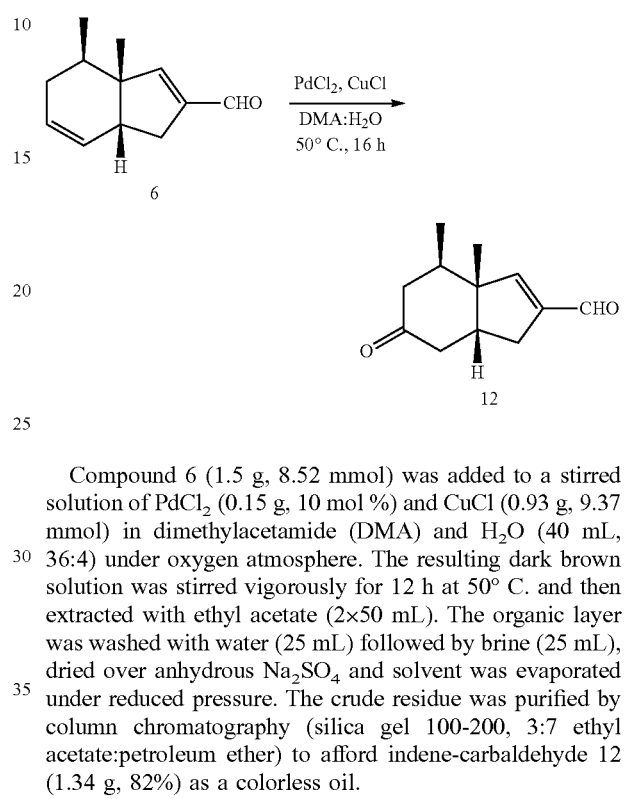

Compound 6 (1.5 g, 8.52 mmol) was added to a stirred solution of PdCl₂ (0.15 g, 10 mol %) and CuCl (0.93 g, 9.37 mmol) in dimethylacetamide (DMA) and H₂O (40 mL, 36:4) under oxygen atmosphere. The resulting dark brown solution was stirred vigorously for 12 h at 50° C. and then extracted with ethyl acetate (2×50 mL). The organic layer was washed with water (25 mL) followed by brine (25 mL), dried over anhydrous Na₂SO₄ and solvent was evaporated under reduced pressure. The crude residue was purified by column chromatography (silica gel 100-200, 3:7 ethyl acetate:petroleum ether) to afford indene-carbaldehyde 12 (1.34 g, 82%) as a colorless oil.

IR$\upsilon_{max}$ (film): 3414, 2963, 1713, 1677, 1457 cm$^{-1}$; $^1$H NMR (400 MHz, CDCl₃) δ 9.76 (s, 1H), 6.77 (s, 1H), 2.89-2.83 (m, 1H), 2.42-2.37 (m, 2H), 2.36-2.34 (m, 1H), 2.29-2.24 (m, 1H), 2.23-2.22 (m, 1H), 2.21-2.20 (m, 1H), 2.15-2.09 (m, 1H), 1.10 (s, 3H), 1.03 (d, J=6.6 Hz, 3H); $^{13}$C NMR (100 MHz, CDCl₃) δ 211.4, 190.3, 158.2, 144.0, 50.86, 44.6, 43.8, 42.9, 34.7, 34.6, 18.8, 16.4 HRMS (ESI) (M+Na)⁺ m/z calcd for C₁₂H₁₆O₂Na⁺ 215.1044, found 215.1043.

Example 5

Synthesis of (3aS,4R,7aR)-2-(hydroxymethyl)-3a,4-dimethyl-4,5,7,7a-tetrahydro-1H-inden-6(3aH)-one (13)

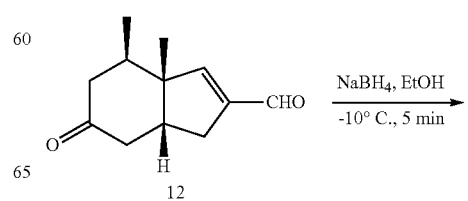

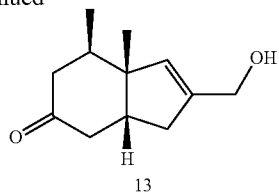

To a solution of 12 (1.3 g, 6.77 mmol) in EtOH (30 mL), was added NaBH$_4$ (128 mg, 3.38 mmol) in portion wise at −10° C. After stirring for 5 min at same temperature, reaction was quenched with saturated aqueous NH$_4$Cl (10 mL). The reaction mixture was extracted with EtOAc (3×50 mL). The combined organic layer was washed with brine (30 mL), dried over Na$_2$SO$_4$, filtered and concentrated in vacuo. Silica gel flash column chromatography (ethyl acetate:petroleum ether, 4:6) afforded the corresponding primary alcohol 13 (1.0 g, 78%) as a colorless oil.

IR$\upsilon_{max}$ (film): 3404, 2958, 2926, 2876, 1711, 1457 cm$^{-1}$; $^1$H NMR (400 MHz, CDCl$_3$) δ 5.62 (s, 1H), 4.16 (s, 2H), 2.68-2.62 (m, 1H), 2.40-2.38 (m, 2H), 2.31-2.24 (m, 1H), 2.17-2.15 (m, 2H), 2.09-2.03 (m, 2H), 1.69-1.67 (m, 1H), 1.03 (s, 3H), 0.95 (d, J=6.7 Hz, 3H); $^{13}$C NMR (100 MHz, CDCl$_3$) δ 213.2, 141.4, 133.3, 62.0, 49.3, 45.2, 44.2, 43.6, 38.9, 35.6, 19.8, 16.4; HRMS (ESI) (M+Na)$^+$ m/z calcd for C$_{12}$H$_{18}$O$_2$Na$^+$ 217.1199, found 217.1199.

Example 6

Synthesis of (3aS,4R,6S,7aR)-2-(hydroxymethyl)-3a,4-dimethyl-3a,4,5,6,7,7a-hexahydro-1H-inden-6-ol (14)

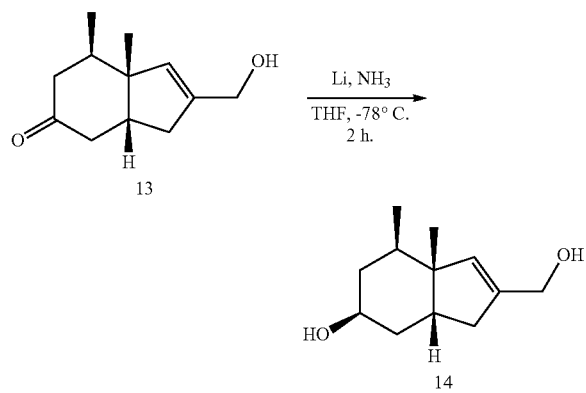

A solution of ketone 13 (1.0 g, 5.62 mmol) in THF (30 mL) was added to liquid ammonia (30 mL) at −78° C. Lithium (0.394 g, 56.28 mmol) was added in small pieces and reaction mixture was stirred at −78° C. for 2 h. After consumption of starting material (by TLC), solid NH$_4$Cl (3.0 g) was added and ammonia was allowed to evaporate at room temperature. Water (20 mL) was added and reaction mixture was extracted with EtOAc (3×50 mL). The combined organic layer was washed with brine (30 mL), dried over Na$_2$SO$_4$, and concentrated. The residue obtained was subjected to silica gel flash column chromatography (ethyl acetate:petroleum ether, 4:6) to afford the diol 14 (0.73 g, 73%) as a colorless oil.

IR$\upsilon_{max}$ (film): 3351, 2921, 1649, 1461 cm$^{-1}$; $^1$H NMR (400 MHz, CDCl$_3$) δ 5.69 (s, 1H), 4.12 (s, 2H), 3.85-3.79 (m, 1H), 2.28-2.12 (m, 3H), 1.96-1.93 (m, 1H), 1.64-1.57 (m, 3H), 1.52-1.45 (m, 2H), 1.16-1.07 (m, 1H), 0.97 (s, 3H), 0.85 (d, J=6.8 Hz, 3H); $^{13}$C NMR (100 MHz, CDCl$_3$) δ 141.8, 136.6, 68.5, 62.4, 48.4, 47.5, 38.9, 36.4, 36.1, 34.4, 17.7, 17.2; HRMS (ESI) (M+Na)$^+$ m/z calcd for C$_{12}$H$_{20}$O$_2$Na$^+$ 219.1356, found 219.1356.

Example 7

Synthesis of (3aS,4R,6S,7aR)-6-hydroxy-3a,4-dimethyl-3a,4,5,6,7,7a-hexahydro-1H-indene-2-carbaldehyde (15)

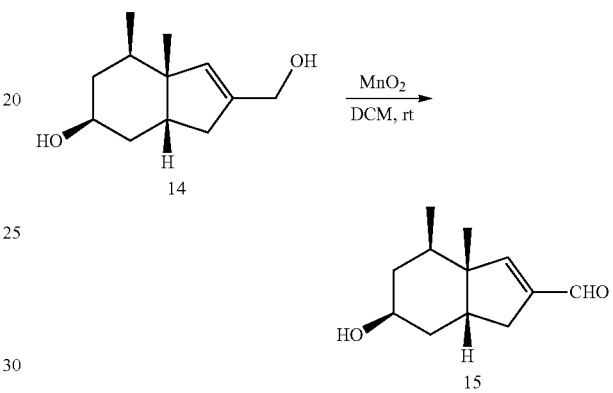

To a stirred solution of 14 (0.70 g, 3.81 mmol) in CH$_2$Cl$_2$ (20 mL) was added MnO$_2$ (3.3 g, 38.1 mmol) at room temperature. The reaction mixture was stirred for 20 h at room temperature (23° C.). After completion of reaction, filtered through a pad of celite and washed with CH$_2$Cl$_2$ and the solvent was removed in vacuo. The crude material obtained after the removal of solvent was purified by column chromatography (silica gel 100-200, 4:6 ethyl acetate:petroleum ether) to afford indene-carbaldehyde 15 (0.64 g, 92%) as a colorless oil. IR$\upsilon_{max}$ (film): 3401, 2959, 2928, 2857, 1681 cm$^{-1}$; $^1$H NMR (400 MHz, CDCl$_3$) δ 9.68 (s, 1H), 6.86 (s, 1H), 3.85-3.81 (m, 1H), 2.58-2.52 (m, 1H), 2.38-2.31 (m, 1H), 2.23-2.17 (m, 1H), 2.01-1.98 (m, 1H), 1.79-1.78 (m, 1H), 1.66-1.62 (m, 1H), 1.56-1.47 (m, 2H), 1.24-1.14 (m, 1H), 1.10 (s, 3H), 0.91 (d, J=6.8 Hz, 3H); $^{13}$C NMR (100 MHz, CDCl$_3$) 190.8, 162.7, 144.8, 67.8, 49.4, 47.7, 38.5, 35.6, 33.9, 32.1, 17.2, 16.8; HRMS (ESI) calcd for C$_{12}$H$_{19}$O$_2$ [M+H]$^+$ 195.1380, found 195.1382.

Example 8

Synthesis of (1aR,1bS,2R,4S,5aS,6aS)-4-hydroxy-1b,2-dimethyloctahydro-6aH-indeno[1,2-b]oxirene-6a-carbaldehyde (16)

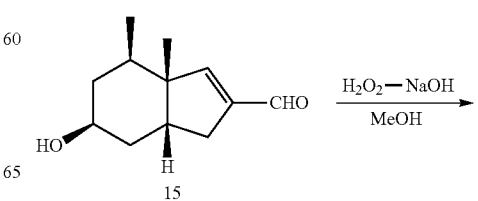

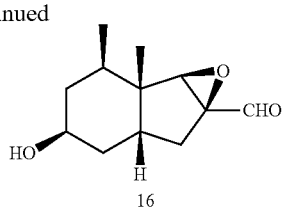

16

Compound 15 (0.52 gm, 2.68 mmol) was dissolved in methanol (10 mL), cooled to 0° C. and added 30% aqueous $H_2O_2$ (0.75 mL, 6.70 mmol) and 6N NaOH (0.26 mL, 1.55 mmol) at 0° C. The reaction mixture was stirred at room temperature (25° C.) for 4 h. The mixture was diluted in diethyl ether (40 mL), washed successively with water (10 mL), brine (10 mL). The organic layer was dried over $Na_2SO_4$, filtered and concentrated in vacuo. The crude material obtained after removal of solvent was pass through small bed silica gel column chromatography (ethyl acetate: petroleum ether 4:6) to give the epoxide 16 (0.394 g, 70%) as colorless oil which is immediately used for next step.

Example 9

Synthesis of (1'R,2R,2'R,3a'R,5'S,7'R,7a'S)-2-methoxy-7',7a'-dimethyl-4-methylenedecahydro-2H-spiro[furan-3,2'-indene]-1',5'-diol (±)-Peribysin E(1)

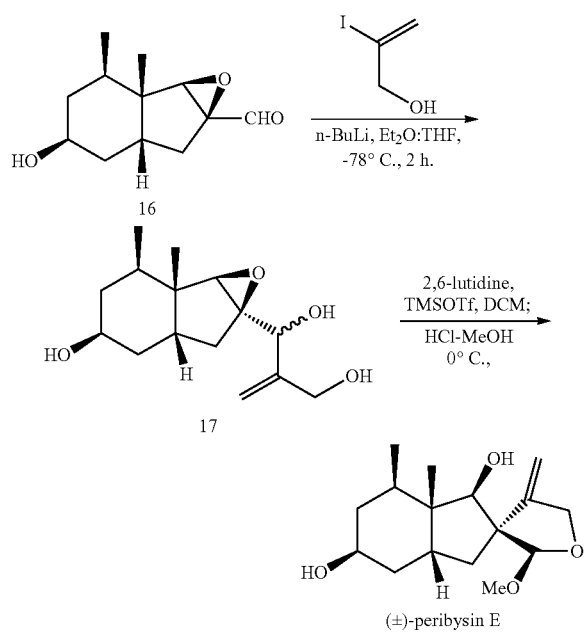

To a solution of n-BuLi (1.9 mL, 2.0 M solution in cyclohexane, 3.81 mmol) in $Et_2O$ (8 mL) at −78° C. was added iodoalcohol (348 mg, 1.90 mmol) in $Et_2O$ (8 mL) dropwise over a period of 30 min with vigorous stirring. A solution of aldehyde 16 (100 mg, 0.47 mmol) in THF (5 mL) was added slowly. The reaction mixture was then stirred for 2 h at same temperature and then quenched with saturated aqueous $NH_4Cl$ (20 mL). The reaction mixture was extracted with EtOAc (3×30 mL). The combined organic layer was washed with brine (20 mL), dried over $Na_2SO_4$, and concentrated. Silica gel flash column chromatography (EtOAc:petroleum ether, 7:3) afforded the diol 17 (41 mg, 54% brsm) as a diastereomeric mixture (colorless oil) which was directly used for next step. To a solution of 17 (40 mg, 0.149 mmol) in anhydrous $CH_2Cl_2$ (10 mL) at 0° C. was added 2,6-lutidine (0.27 mL, 2.38 mmol) followed by TMSOTf (0.21 mL, 1.19 mmol). Reaction mixture was stirred for 30 min at same temperature and then quenched with saturated $NaHCO_3$ (10 mL). The reaction mixture was extracted with $CH_2Cl_2$ (3×10 mL). The combined organic layer was washed with brine (10 mL), dried over $Na_2SO_4$ and concentrated to give crude product. To a solution of the crude product in MeOH (10 mL) at 0° C. was added 35% HCl (0.02 mL). The reaction mixture was stirred for 1 h and then quenched with saturated $NaHCO_3$ (10 mL). The reaction mixture was extracted with EtOAc (3×15 mL). The combined organic layer was washed with brine (15 mL), dried over $Na_2SO_4$, and concentrated which on silica gel flash column chromatography (ethyl acetate:petroleum ether, 1:2) afforded (±)-peribysin E (25 mg, 62%) as a colorless oil.

IR$\upsilon_{max}$ (film): 3404, 2923, 2926, 2864, 1655, 1263 cm$^{-1}$; $^1$H NMR (500 MHz, CDCl$_3$) δ 5.08 (s, 1H), 4.98 (t, J=1.83 Hz, 1H), 4.94 (t, J=2.4 Hz, 1H), 4.49 (dt, J=13.1, 2.4 Hz, 1H), 4.47 (dt, J=12.9, 2.4 Hz, 1H), 3.94-3.88 (m, 1H), 3.56 (d, J=2.1 Hz, 1H), 3.38 (s, 3H), 2.19 (d, J=2.7 Hz, 1H), 2.03-1.97 (m, 1H), 1.94 (ddt, J=13.4, 4.5, 2.4 Hz, 1H), 1.88 (dd, J=13.1, 5.8 Hz, 1H), 1.78-1.75 (m, 1H), 1.72-1.68 (m, 1H), 1.64-1.63 (m, 1H), 1.57-1.55 (m, 1H), 1.54-1.48 (m, 1H), 1.30-1.21 (m, 1H), 0.92 (s, 3H), 0.86 (d, J=6.8 Hz, 3H); $^{13}$C NMR (125 MHz, CDCl$_3$) δ 152.7, 105.7, 103.2, 88.7, 69.1, 67.2, 60.9, 55.2, 45.9, 40.1, 35.5, 34.3, 33.0, 16.2, 14.5; HRMS (ESI) (M+Na)$^+$ m/z calcd for $C_{16}H_{26}O_4Na^+$ 305.1721, found 305.1723.

Example 10

Synthesis of (1aR,1bS,2R,5aR,6aS)-1b,2-dimethyl-1b,2,3,5a,6,6a-hexahydro-1aH-indeno[1,2-b]oxirene-6a-carbaldehyde (7)

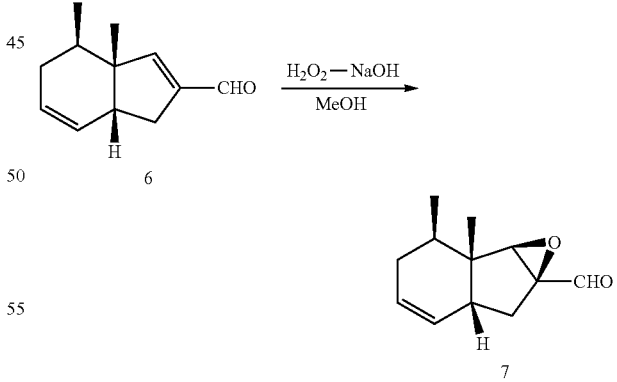

To a solution of the α,β-unsaturated aldehyde 6 (1.0 g, 5.68 mmol) in 10 mL of methanol was added 30% aqueous $H_2O_2$ (1.8 mL, 14.20 mmol) and 6N NaOH (0.46 mL, 3.29 mmol) at 0° C. The reaction was stirred at rt. for 4 h. The mixture was diluted in ether (3×50 mL), washed successively with water, brine, dried, concentrated, and purified by silica gel chromatography to give the epoxide 7 (780 mg, 74%) as colorless oil.

IR$\upsilon_{max}$ (film): 3393, 3022, 2964, 2884, 2835, 1721, 1454 cm$^{-1}$.

$^1$H NMR (400 MHz, CDCl3) δ 9.19 (s, 1H), 5.64-5.63 (m, 2H), 3.71 (s, 1H) 2.21-2.18 (m, 1H), 1.97-1.87 (m, 3H), 1.76-1.69 (m, 1H), 1.52-1.47 (m, 1H), 1.0 (s, 3H), 0.97 (d, J=6.8 Hz, 3H).

$^{13}$C NMR (100 MHz, CDCl$_3$) δ 197.5, 126.7, 125.9, 68.5, 67.5, 42.8, 40.8, 30.7, 30.4, 29.5, 15.5, 14.1.

HRMS (ESI) talc for C$_{12}$H$_{16}$O$_2$Na$^+$ 215.1041, found 215.1043.

Example 11

Synthesis of v1-((1aR,1bS,2R,5aR,6aR)-1b,2-dimethyl-1b,2,3,5a,6,6a-hexahydro-1aH-indeno[1,2-b]oxiren-6a-yl)-2-methylenepropane-1,3-diol (8)

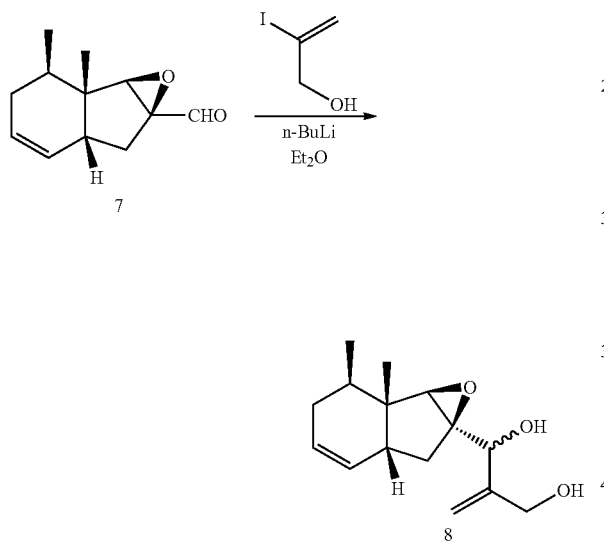

To a solution of n-BuLi (7.8 mL, 2.0 M solution in cyclohexane, 15.6 mmol) in Et$_2$O (15 mL) at −78° C. was added iodoalcohol (1.42 g, 7.8 mmol) in Et$_2$O (15 mL) over a period of 0.5 h. A solution of aldehyde 7 (0.5 g, 2.6 mmol) in Et$_2$O (10 mL) was added. The reaction mixture was stirred, for 2 h and then quenched with saturated aqueous NH$_4$Cl (25 mL). The reaction mixture was extracted with EtOAc (3×50 mL). The combined organic layer was washed with brine (30 mL), dried over Na$_2$SO$_4$, and concentrated. Silica gel flash column chromatography (EtOAc/hexane, 1:2) afforded the diol 8 (0.395 g, 61% based on 7 recovered) as a diastereomeric mixture (colorless oil). One diastereomer (Rf=0.2) was isolated with silica gel flash column chromatography (EtOAc/hexane, 1:2).

IR (film) v 3393, 3019, 2400, 1616, 1454, 1384, 1208, 1036 cm-1;

$^1$H NMR (400 MHz, CDCl$_3$) δ 5.60-5.59 (m, 2H) 5.25 (d, J=1.2 Hz, 1H), 5.16 (dd, J=0.9 Hz, 1H), 4.50 (s, 1H), 4.25 (d, J=13.5 Hz, 1H), 4.12 (d, J=14.1 Hz, 1H), 3.47 (s, 1H), 2.89 (s, 1H), 2.76 (s, 1H), 2.53 (s, 1H), 2.13-2.07 (m, 1H), 1.93-1.86 (m, 2H), 1.75-1.68 (m, 1H), 1.51-1.44 (m, 2H), 0.92 (d, J=6.6 Hz, 3H), 0.93 (s, 3H).

$^{13}$C NMR (100 MHz, CDCl$_3$) δ 146.2, 127.4, 125.7, 115.4, 73.2, 68.7, 66.9, 63.7, 42.3, 41.5, 33.4, 30.5, 30.0, 15.5, 13.6.

HRMS (ESI) (M+Na)$^+$ m/z calcd for C$_{15}$H$_{22}$O3Na 273.1464, found 273.1461.

Example 12

Synthesis of (2R,2'R,3'R,3a'S,4'R,7a'R)-2-methoxy-3a',4'-dimethyl-4-methylene 1',3',3a',4,4',5,5',7a'-octahydro-2H-spiro[furan-3,2'-inden]-3'-ol (9)

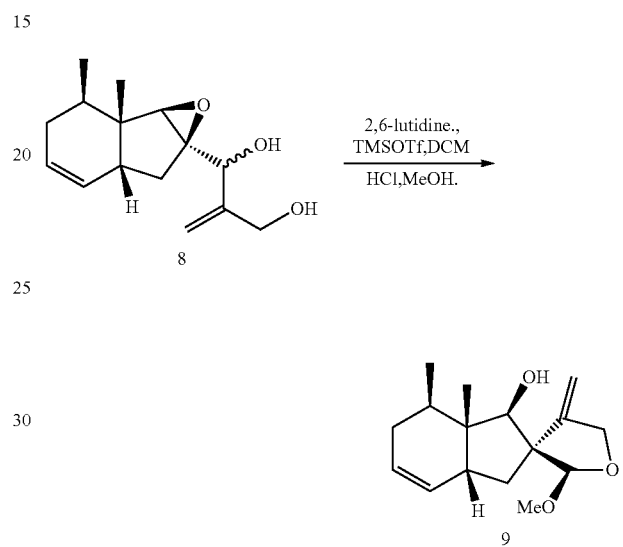

To a solution of 8 (160 mg, 0.640 mmol) in anhydrous CH$_2$Cl$_2$ (20 mL) at 0° C. were added 2,6-lutidine (1.1 mL, 8.96 mmol) and TMSOTf (0.89 mL, 4.48 mmol). After stirring for 0.5 h, saturated NaHCO$_3$ (20 mL) was added. The reaction mixture was extracted with CH$_2$Cl$_2$ (3×30 mL). The combined organic layer was washed with brine (15 mL) and dried over Na$_2$SO$_4$. Concentration gave the crude product. To a solution of the crude product in MeOH (25 mL) was added 35% HCl (0.5 mL). The reaction mixture was stirred for 0.5 h and then quenched with saturated NaHCO$_3$ (15 mL). The reaction mixture was extracted with EtOAc (3×30 mL). The combined organic layer was washed with brine (15 mL), dried over Na$_2$SO$_4$, and concentrated. Silica gel flash column chromatography (EtOAc/hexane, 1:2) afforded 9 (108 mg, 64%) as a colorless oil.

IR$\upsilon_{max}$ (film): 3478, 3017, 2959, 2927, 1660, 1452, 1360, 1202, 1098, 1042, 999, 939 cm$^{-1}$.

$^1$H NMR (400 MHz, CDCl$_3$) δ 5.71-5.62 (m, 2H), 5.12 (s, 1H), 5.00 (t, J=2. Hz, 1H), 4.96 (t, J=2.4 Hz, 1H), 4.49 (dt, J=11.3, 2.4 Hz, 1H), 4.41 (dt, J=11.2, 2.7 Hz, 1H), 4.03-4.01 (m, 1H), 3.60 (d, J=3.4 Hz, 1H), 3.40 (s, 3H), 2.15 (d, J=3.9 Hz, 1H), 2.10-2.06 (m, 2H), 1.98-1.92 (m, 1H), 1.85-1.82 (m, 1H), 1.56-1.51 (m, 1H), 1.44-1.39 (m, 1H), 0.93 (d, J=6.7 Hz, 3H), 0.87 (s, 3H).

$^{13}$CNMR (100 MHz, CDCl$_3$) δ 152.1, 128.7, 126.0, 105.6, 103.4, 90.2, 69.0, 60.4, 55.1, 46.8, 44.4, 35.6, 34.7, 30.8, 15.2.

HRMS (ESI) (M+Na)$^+$ m/z calcd for C$_{16}$H$_{24}$O$_3$Na=287.1609, found 287.1618.

Example 13

Synthesis of 7(1a'R,2R,3R,3'R,3a'S,4'R,6a'S,6b'S)-2-methoxy-3',3a'-dimethyl-4-methylenedecahydro-2H-spiro[furan-3,5'-indeno[4,5-b]oxiren]-4'-ol (10)

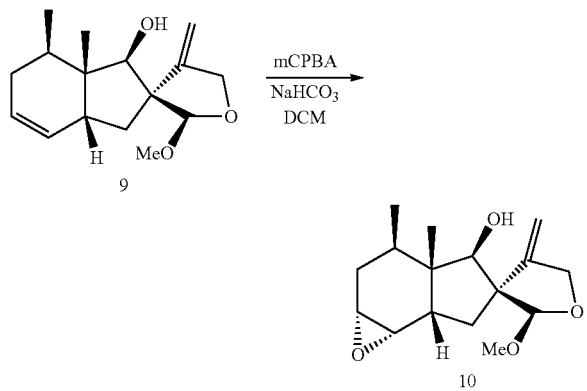

To a stirred solution of 9 (170 mg, 0.653 mmol) in DCM (20 mL) and 15% NaHCO$_3$ (1.7 mL, 3.21 mmol) at 0° C. was added mCPBA (132 mg, 0.772 mmol) in portions. The mixture was stirred at 0° C. for 1 h and filtered. The filtrate was washed successively with saturated aqueous NaHCO$_3$ (10 mL), H$_2$O (10 mL) then with brine (10 mL). The organic layer was dried (Na$_2$SO$_4$), filtered and evaporated to give a solid, which was purified by Silica gel flash column chromatography (EtOAc/pet.ether, 2:8) afforded 10 (128 mg, 72%) as a white solid.

Mp: 82-84° C.

IR$\upsilon_{max}$ (film): 3435, 2928, 1661, 1452, 1197, 1097, 1055 cm$^{-1}$.

$^1$H NMR (400 MHz, CDCl$_3$) δ 5.05 (s, 1H), 55.01 (m, 2H), 4.49 (dt, J=13.2, 2.1 Hz, 1H), 4.42 (dt, J=13.1, 2.4 Hz, 1H), 3.45 (d, J=3.17 Hz, 1H), 3.40 (s, 3H), 3.27-3.26 (m, 1H), 3.17-3.15 (m, 1H) 2.14 (d, J=3.9 Hz, 1H), 2.05-2.00 (m, 1H), 1.93-1.88 (m, 2H), 1.77-1.71 (m, 1H), 1.65-1.63 (m, 1H) 0.88-0.83 (m, 6H).

$^{13}$CNMR (100 MHz, CDCl$_3$) δ 151.4, 105.4, 103.8, 90.8, 69.3, 59.4, 55.2, 53.4, 53.2, 44.7, 42.7, 32.5, 30.2, 29.52, 16.1, 14.9.

HRMS (ESI) (M+Na)$^+$ m/z calcd for C$_{16}$H$_{24}$O$_4$Na=303.1564, found 305.1567.

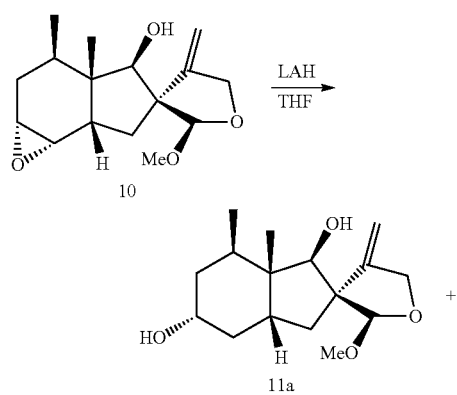

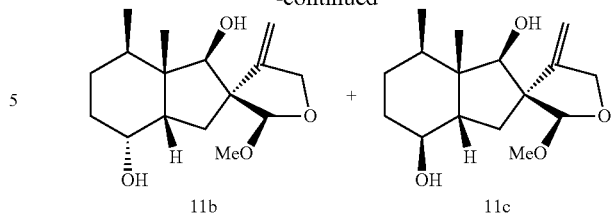

To a stirred suspension of LiAlH$_4$ (0.135 g, 3.57 mmol) in dry THF (10 mL) was slowly added a solution of epoxide 10 (0.125 g, 0.446 mmol) in dry THF (10 mL) under an atmosphere of nitrogen at 25° C. The resulting suspension was heated at reflux for 2 h, and then allowed to cool to 25° C. EtOAc (20 mL) was added followed by saturated aqueous NH$_4$Cl (10 mL). The organic layer was separated, dried over Na$_2$SO$_4$ and evaporated. The crude was purified by MPLC (combiflash rf) column chromatography (EtOAc:Pet.Ether, 3:7) afforded three product 11a, 11b and 11c (115 mg, 92%) as a colorless oils. Structures are assigned tentatively based NMR data.

(1'R,2R,2'R,3a'R,5'R,7'R,7a'S)-2-methoxy-7',7a'-dimethyl-4-methylene decahydro-2H-spiro[furan-3,2'-indene]-1',5'-diol (11a)

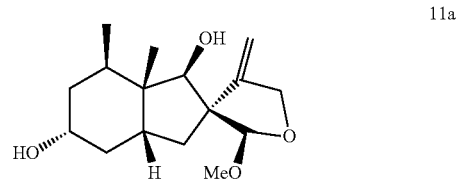 [SMILES: C=C1CO[C@@H](OC)[C@]12C[C@@H]1C[C@H](O)C[C@@H](C)[C@]1(C)[C@H]2O]

IR$\upsilon_{max}$ (film): 3401, 2926, 1661, 1459, 1099, 1044 cm$^{-1}$.

$^1$H NMR (400 MHz, CDCl$_3$) δ 5.10 (s, 1H), 5.01 (m, 2H), 4.49 (dt, J=13.0, 2.2 Hz, 1H), 4.40 (dt, J=13.2, 2.2 Hz, 1H), 3.95-3.90 (m, 1H), 3.59 (d, J=2.2 Hz, 1H), 3.36 (s, 3H), 2.21-2.15 (m, 2H), 2.02-1.97 (m, 1H), 1.87 (m, 1H), 1.78-1.74 (m, 1H), 1.63-1.60 (m, 2H), 1.58-1.50 (m, 1H), 1.46-1.41 (m, 1H), 1.31-1.27 (m, 1H), 0.92 (s, 3H), 0.79 (d, J=6.3 Hz, 3H).

$^{13}$CNMR (100 MHz, CDCl$_3$) δ 152.8, 105.8, 103.4, 88.2, 69.4, 69.0, 60.5, 55.3, 51.3, 48.9, 34.6, 30.0, 29.2, 27.0, 15.8, 14.9.

HRMS (ESI) (M+Na)$^+$ m/z calcd for C$_{16}$H$_{26}$O$_4$Na=305.1720, found 305.1723.

(1'R,2R,2'R,3a'S,4'R,7'R,7a'S)-2-methoxy-7',7a'-dimethyl-4-methylenedecahydro-2H-spiro[furan-3,2'-indene]-1',4'-diol (11b)

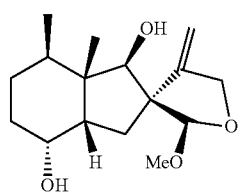

IR$\upsilon_{max}$ (film): 3411, 2926, 1661, 1459, 1099, 1045 cm$^{-1}$.

$^1$H NMR (400 MHz, CDCl$_3$) δ 5.09 (s, 1H), 5.04 (t, J=2.4 Hz, 1H), 4.9 (t, J=2.1 Hz, 1H) 4.48 (dt, J=13.0, 2.3 Hz, 1H), 4.39 (dt, J=13.2, 2.4 Hz, 1H), 4.03-4.01 (m, 1H), 3.68 (d, J=2.2 Hz, 1H), 3.38 (s, 3H), 2.21 (d, J=2.7 Hz 1H), 2.08-2.03 (m, 1H), 1.87-1.74 (m, 1H), 1.61-1.54 (m, 3H), 1.40 (m, 1H) 0.89 (m, 6H).

$^{13}$CNMR (100 MHz, CDCl$_3$) δ 152.9, 106.0, 103.6, 88.9, 69.0, 66.9, 60.9, 55.2, 46.0, 42.9, 37.6, 35.2, 34.5, 31.6, 16.3, 15.7.

HRMS (ESI) (M+Na)$^+$ m/z calcd for C$_{16}$H$_{26}$O$_4$Na=305.1722, found 305.1723.

(1'R,2R,2'R,3a'S,4'S,7'R,7a'S)-2-methoxy-7',7a'-dimethyl-4-methylenedecahydro-2H-spiro[furan-3,2'-indene]-1',4'-diol (11c)

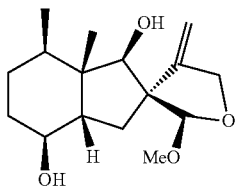

11c

IRυ$_{max}$ (film): 3401, 2926, 1661, 1459, 1099, 1044, 757 cm$^{-1}$.

$^1$H NMR (400 MHz, CDCl$_3$) δ 5.11 (s, 1H), 5.0 (m, 2H), 4.50 (dt, J=13.1, 1.9 Hz, 1H), 4.41 (dt, J=13.3, 2.2 Hz, 1H), 3.86-3.82 (m, 1H), 3.62 (d, J=2.1 Hz, 1H), 3.39 (s, 3H), 2.17 (d, J=2.2 Hz 1H), 2.09-2.04 (m, 1H), 1.80-1.76 (m, 1H), 1.68-1.62 (m, 1H), 1.55-1.1.53 (m, 2H), 1.45-1.41 (m, 1H), 1.29-1.25 (m, 1H), 1.09 (s, 3H), 0.88 (d, J=6.1 Hz, 3H).

$^{13}$CNMR (100 MHz, CDCl$_3$) δ 152.9, 106.0, 103.5, 89.2, 70.6, 69.1, 59.9, 55.3, 51.7, 46.9, 36.1, 32.2, 29.8, 27.7, 17.4, 16.3.

HRMS (ESI) (M+Na)$^+$ m/z calcd for C$_{16}$H$_{26}$O$_4$Na=305.1720, found 305.1723.

Example 14

Synthesis of (1aR,1bS,2R,5aS,6aS)-1b,2-dimethyl-octahydro-1aH-indeno[1,2-b]oxirene-6a-carbaldehyde (18)

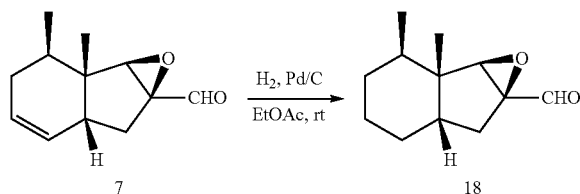

To a solution of 7 (100 mg, 0.52 mmol) in EtOAc (10 mL) was added Pd/C (10 mg) and the mixture was stirred under hydrogen balloon pressure. After 1 h catalyst was filtered off and concentrated to afford 18 (96 mg, 95%) as colorless oil.

IRυ$_{max}$ (film): 2960, 2928, 2857, 1721, 1461 cm$^{-1}$; $^1$H NMR (400 MHz, CDCl$_3$) δ 9.20 (s, 1H), 3.62 (s, 1H), 2.20-2.14 (m, 1H), 1.82-1.76 (m, 1H), 1.64-1.60 (m, 1H), 1.54-1.47 (m, 3H), 1.39-1.31 (m, 2H), 1.29-1.18 (m, 2H), 1.04 (s, 3H), 0.88 (d, J=6.4 Hz, 3H). $^{13}$C NMR (100 MHz, CDCl$_3$) δ 198.5, 68.6, 67.7, 42.8, 37.9, 32.9, 29.9, 26.5, 22.9, 21.4, 17.0, 14.0. HRMS (ESI) calc for C$_{12}$H$_{18}$O$_2$Na$^+$ 217.1195, found 217.1199.

Example 15

Synthesis of 1-((1aR,1bS,2R,5aS,6aR)-1b,2-dimethyloctahydro-1aH-indeno[1,2-b]oxiren-6a-yl)-2methylenepropane-1,3-diol (19)

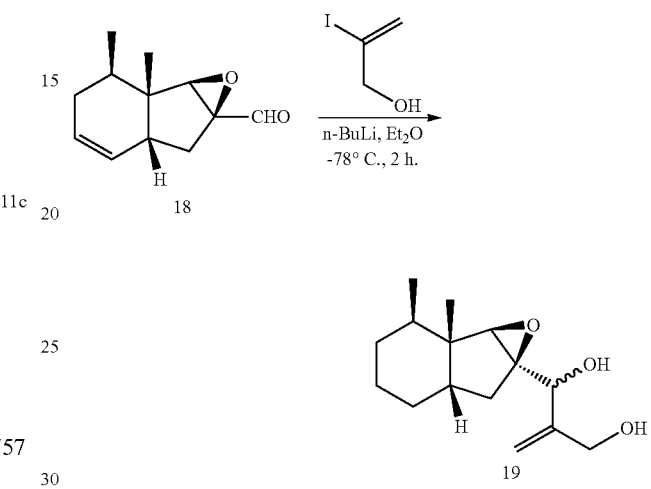

Compound 19 was synthesized using the procedure similar to preparation of 8. IRυ$_{max}$ (film): 3368, 2925, 1649, 1458, 1034 cm$^{-1}$; $^1$H NMR (400 MHz, CDCl$_3$) δ 5.27 (d, J=1.2 Hz, 1H), 5.18 (d, J=0.9 Hz, 1H), 4.55 (s, 1H), 4.29 (d, J=13.5 Hz, 1H), 4.14 (d, J=14.1 Hz, 1H), 3.39 (s, 1H), 1.79-1.71 (m, 2H), 1.69-1.63 (m, 2H), 1.48-1.45 (m, 3H), 1.37-1.33 (m, 1H), 1.23-1.20 (m, 1H), 1.08-1.02 (m, 1H), 0.98 (s, 3H), 0.89 (d, J=7 Hz, 3H); $^{13}$C NMR (100 MHz, CDCl$_3$) δ 146.5, 115.1, 73.6, 68.1, 67.6, 63.9, 42.3, 38.5, 33.5, 30.0, 23.2, 23.1, 21.7, 17.0, 14.0; HRMS (ESI) (M+Na)$^+$ m/z calcd for C$_{15}$H$_{24}$O$_3$Na$^+$ 275.1464, found 275.1461.

Example 16

Synthesis of (1'R,2R,2'R,3a'S,7'R,7a'S)-2-methoxy-7',7a'-dimethyl-4-methylenedecahydro-2H-spiro[furan-3,2'-inden]-1'-ol (20)

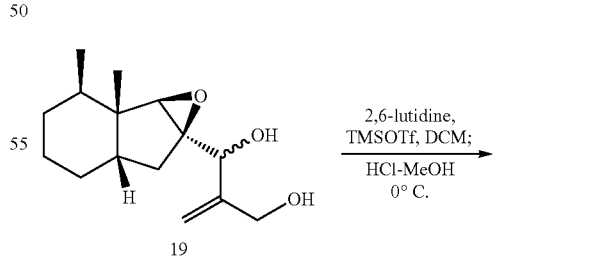

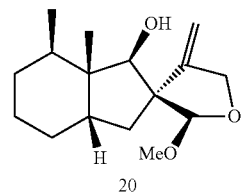

Compound 20 was synthesized using the procedure similar to preparation of 9. IR$\upsilon_{max}$ (film): 3401, 2926, 1661, 1462, 1038 cm$^{-1}$; $^1$H NMR (400 MHz, CDCl$_3$) δ 5.09 (s, 1H), 5.00 (t, J=2.4 Hz, 1H), 4.98 (t, J=1.8 Hz, 1H), 4.49 (dt, J=10.7, 2.4 Hz, 1H), 4.41 (dt, J=10.7, 2.1 Hz, 1H), 3.59 (d, J=3.2 Hz, 1H), 3.38 (s, 3H), 2.12 (d, J=2.1 Hz, 1H), 1.87-1.82 (m, 2H), 1.80-1.79 (m, 1H), 1.61-1.57 (m, 2H), 1.52-1.41 (m, 4H), 1.21-1.18 (m, 1H), 0.90 (s, 3H), 0.80 (d, J=6.7 Hz, 3H); $^{13}$C NMR (100 MHz, CDCl$_3$) δ 152.2, 106.1, 103.1, 89.1, 69.1, 60.6, 55.2, 46.6, 44.8, 35.8, 32.2, 30.5, 25.1, 21.3, 16.5, 14.9; HRMS (ESI) (M+Na)$^+$ m/z calcd for C$_{16}$H$_{26}$O$_3$Na$^+$ 289.1609, found 289.1618.

Example 17

Synthesis of (1'R,2R,2'R,3a'S,7'R,7a'S)-2-methoxy-7',7a'-dimethyl-4-methylenedecahydro-2H-spiro[furan-3,2'-indene]-1',4',5'-triol (21 and 22)

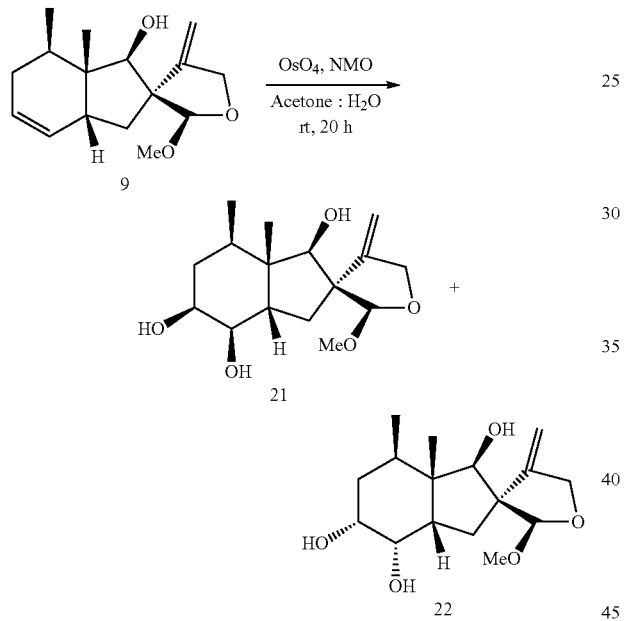

To a solution of alkene 9 (60 mg, 0.227 mmol) in an 4:1 acetone:water mixture (12 mL) were added NMO.H$_2$O (110 mg, 0.91 mmol) and a 2.5% solution of OsO$_4$ in t-BuOH (0.1 mL, 0.01 mmol). The mixture was stirred at room temperature (25° C.) for 24 h, followed by addition of NaHSO$_3$ (10 mg) and further stirring for 30 min. The acetone was removed under reduced pressure, brine was added and the aqueous layer was extracted with EtOAc (3×30 mL). The combined organic layer was dried over Na$_2$SO$_4$, and concentrated in vacuo. Silica gel flash column chromatography of the residue using ethyl acetate:petroleum ether, 7:3 afforded 21 and 22 as inseparable mixture (58 mg, 88%) as a colorless oil.

IR$\upsilon_{max}$ (film): 3418, 2927, 1645, 1040 cm$^{-1}$; $^1$H NMR (400 MHz, CDCl$_3$) δ 5.10 (s, 1H), 5.04-4.93 (m, 2H), 4.50-4.38 (m, 1H), 4.40 (dt, J=13.2, 2.2 Hz, 1H), 4.02-3.76 (m, 2H), 3.63 (s, 1H), 3.39 (s, 3H), 2.21-2.14 (m, 2H), 2.08-2.04 (m, 1H), 1.98-1.93 (m, 1H), 1.77-1.71 (m, 1H), 1.61-1.45 (m, 2H), 1.05 (s, 2H), 0.90-0.82 (m, 5H); $^{13}$CNMR (100 MHz, CDCl$_3$) δ 152.3, 105.4, 103.7, 90.0, 71.6, 70.1, 69.6, 60.5, 55.3, 51.7, 45.3, 37.3, 31.0, 29.8 16.6, 16.0; HRMS (ESI) (M+Na)$^+$ m/z calcd for C$_{16}$H$_{26}$O$_4$Na$^+$ 321.1720, found 321.1723.

Example 18

Biological Assay
Determination of Cell Adhesion Inhibition

An 8 point dose dependent assay was carried out to assess the IC$_{50}$'s of the test compounds.

10,000 HUVEC cells/well (passage number. 8) was seeded into a 96 well black clear bottom plate and cells were cultured for 4 days at 37° C. After the cell culture, HUVEC's were dosed with test compound and reference compound (peribysin E) at a top concentration of 100 μM (1:3 step down dilution-8 concentrations) and cells were cultured for 2 hours at 37° C. HUVEC's were treated with/without 100 ng/mL of TNF-α further cultured for 4 hours at 37° C. 100,000 HL60 cells/well (passage number. 16) was loaded with Calcein AM dye and co-cultured with HUVECs, and cells were cultured for 30 mins at 37° C. HL60-HUVEC cell adhesion was detected by a fluorometric method using a BMG Polarstar. (IC50=inhibition concentration at 50%).

HL60-HUVEC Cell Adhesion-IC$_{50}$ Assessment of Compound

| Sr NO. | Compound | IC$_{50}$ μM |
|---|---|---|
| 1 | 9 | 18.7 |
| 2 | 10 | 15.8 |
| 3 | 11a | 10.4 |
| 4 | 11b | 4.28 |
| 5 | 11c | 13.8 |
| 6 | 20 | 11 |
| 7 | Mixture (21 and 22) | 2.23 |
| 8 | Peribysin E | 6.9-12.2 |

Advantages of Invention

The instant process is simple, cost-effective and time saving. Further the products obtained by the process are pure with good yield.

No protecting group was used in the entire sequence. The present route is flexible, faster, and capable of producing several analogues of the natural product Peribysin E).

We claim:
1. A compound of formula I

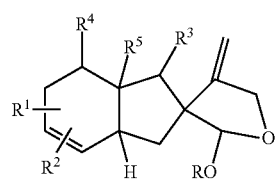

wherein;
R is hydrogen or (C1-C8) alkyl,
R$^1$ and R$^2$ each are individually selected from the group consisting of H, OH, OR or R$^1$ and R$^2$ together may form a 4-8 membered alicyclic, or an aromatic ring which may additionally contain a hetero atom, or R$^1$ and R$^2$ together form an epoxide ring, wherein when the bond between the carbon atoms to which R$^1$ and R$^2$ are attached is a single bond, a hydrogen atom is attached to each of the carbon atoms;

$R^3$ is OH and the carbon atom to which $R^3$ is attached is also attached to a hydrogen atom;

$R^4$ and $R^5$ are selected from hydrogen, C1-C8 alkyl, $CONR^2$, COOR; or $R^4$ and $R^5$ may form a 4-8 membered alicyclic ring which may additionally contain a heteroatom, wherein the compound is not (±)-Peribysin E.

2. The compound as claimed in claim 1, wherein said compound exhibits cell adhesion inhibition activity wherein the inhibition concentration at 50% ($IC_{50}$) is in the range of 2.0-20.0 μM.

3. The compound as claimed in claim 1, wherein the compound is:

(2R,2'R,3'R,3a'S,4'R,7a'R)-2-methoxy-3a',4'-dimethyl-4-methylene 1',3',3a',4,4', 5,5',7a'-octahydro-2H-spiro [furan-3,2'-inden]-3'-ol (9);

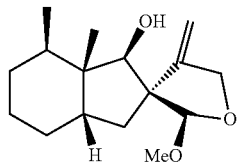

(1a'R,2R,3R,3'R,3a'S,4'R,6a'S,6b'S)-2-methoxy-3',3a'-dimethyl-4-methylenedecahydro-2H-spiro[furan-3,5'-indeno[4,5-b]oxiren]-4'-ol (10);

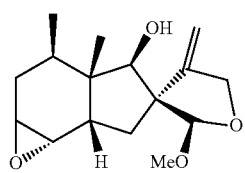

(1'R,2R,2'R,3a'R,5'R,7'R,7a'S)-2-methoxy-7',7a'-dimethyl-4-methylene decahydro-2H-spiro[furan-3,2'-indene]-1',5'-diol (11a);

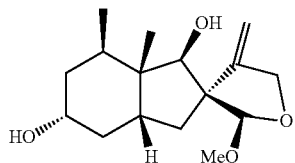

(1'R,2R,2'R,3a'S,4'R,7'R,7a'S)-2-methoxy-7',7a'-dimethylenedecahydro-2H-spiro [furan-3,2'-indene]-1',4'-diol (11b);

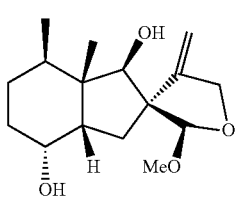

(1'R,2R,2'R,3a'S,4'S,7'R,7a'S)-2-methoxy-7',7a'-dimethyl-4-methylenedecahydro-2H-spiro [furan-3,2'-indene]-1',4'-diol (11c):

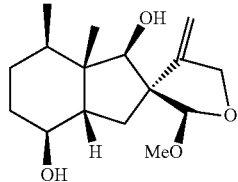

(1'R,2R,2'R,3a'S,7'R,7a'S)-2-methoxy-7',7a'-dimethyl-4-methylene decahydro-2H-spiro [furan-3,2'-inden]-1'-ol (20);

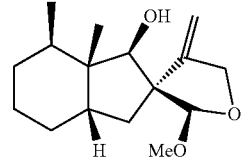

(1'R,2R,2'R,3a'S,7'R,7a'S)-2-methoxy-7',7a'-dimethyl-4-methylene decahydro-2H-spiro[furan-3,2'-indene]-1',4',5'-triol (21); or

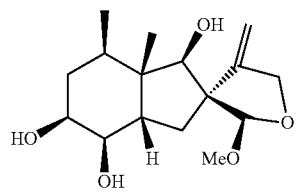

or (1'R,2R,3R,3a'S,4'S,5'R,7'R,7a'S)-2-methoxy-7',7a'-dimethyl-4-methylenedecahydro-2H-spiro[furan-3,2'-indene]-1',4',5'-triol (22):

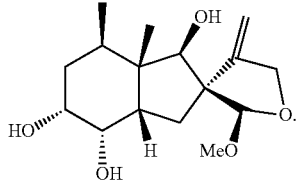

4. A process for the preparation of a compound of formula-I, according to claim 1, or (±)-Peribysin E, comprising:

o) reacting a compound of formula-II with a compound of formula-III in the ratio ranging between 1 to 2.5 in the presence of $BF_3.Et_2O$ in a suitable organic solvent at a temperature in the range of −78 to 25° C. to obtain a compound of formula-IV, $R^4$ and $R^5$ are methyl;

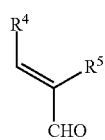

Formula-II

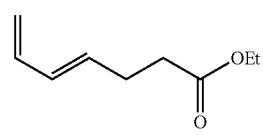

Formula III

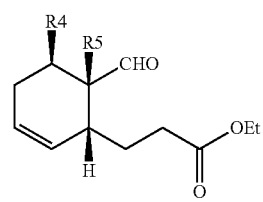

Formula IV p) reducing the compound of formula IV with lithium aluminum hydride (LAH) in a ratio ranging between 1 to 4 in presence of an organic solvent to obtain a diol compound (4) followed by oxidizing in presence of a Collins reagent to obtain a corresponding aldehyde, compound (5)

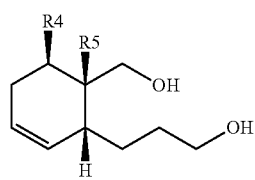

4

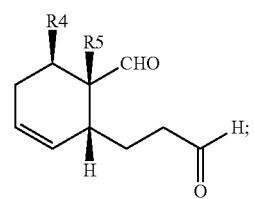

5 q) subjecting compound (5) to an intramolecular aldol reaction in presence of an aqueous metal hydroxide and an alcohol to obtain an intermediate, compound (6)

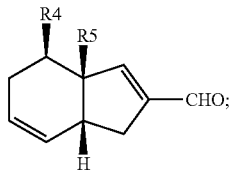

6 r) oxidizing compound (6) under regioselective Wacker conditions to obtain a keto-aldehyde (12) followed by selective reduction at a temperature in the range of −80° C. to 0° C. to obtain an alcohol, compound (13)

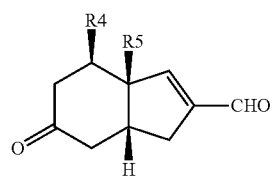

12

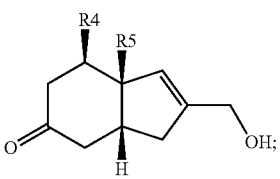

13 s) subjecting compound (13) to reduction in presence of a lithium amide to obtain an alcohol, compound (14), followed by oxidizing to obtain an α,β-unsaturated aldehyde, compound (15), using $MnO_2$; subsequently epoxidising compound (15) to obtain a corresponding epoxide, compound (16), which is further treated with an iodoalcohol of the formula:

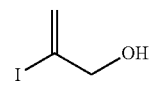

to obtain a diastereomeric mixture of compound (17)

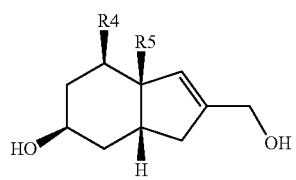

14

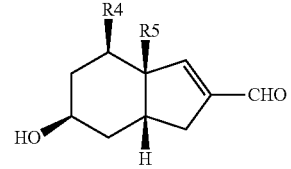

15

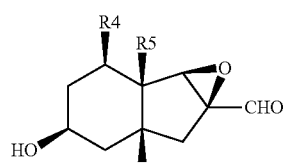

16

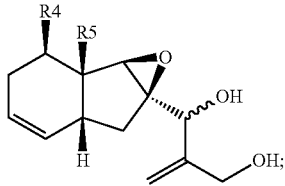

8 v) treating compound (8) with 2,6-lutidine and TMSOTf followed by reacting with methanolic HCl to obtain crude compound (9)

17

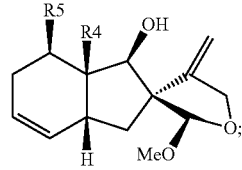

9

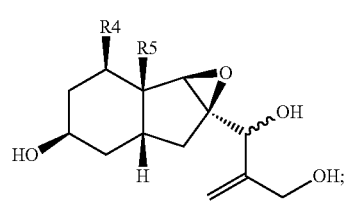

and t) treating compound (17) with 2,6-lutidine and TMSOTf followed by reacting with methanolic HCl to obtain crude Peribysin E; optionally purifying the crude Peribysin E w) epoxidising compound (9) in presence of mCPBA to obtain compound (10);

x) reducing oxirane compound (10) in presence of lithium aluminium hydride, to obtain three stereoisomers (11a), (11b) and (11c)

Peribysin E

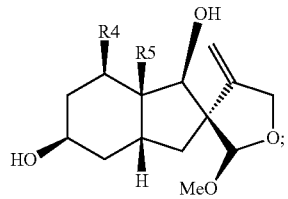

(10)

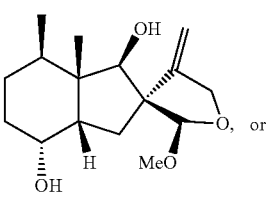

u) epoxidising intermediate compound (6) as obtained in step q, to obtain oxirene-carbaldehyde compound (7)

7

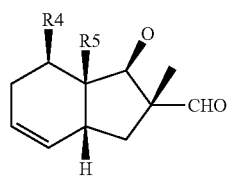

(11a)

(11b)

(11c)

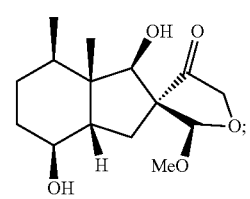

followed by reacting compound (7) with the iodoalcohol of the formula

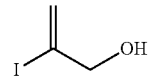

to obtain a diastereomeric mixture of compound (8)

y) hydrogenating oxirene-carbaldehyde intermediate compound (7) as obtained in step

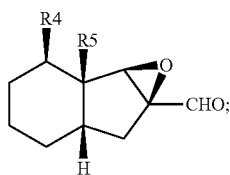

(u), to obtain saturated hydrindane (18)

z) reacting compound (18) with the iodoalcohol of the formula:

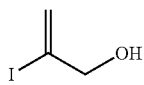

to obtain a diastereomeric mixture of compound (19)

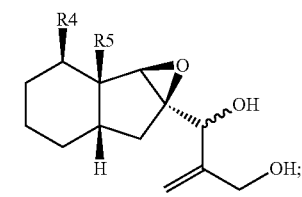

aa) treating compound (19) with 2,6-lutidine and TMSOTf, followed by reacting with methanolic HCl, to obtain compound (20)

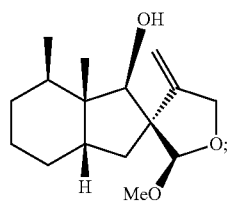

and bb) subjecting compound (9) as obtained in step v) to dihydroxylation in presence of OsO$_4$-catalyst to furnish mixture of triols (21) and (22)

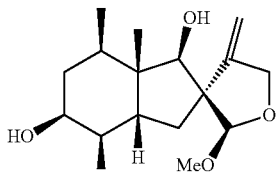

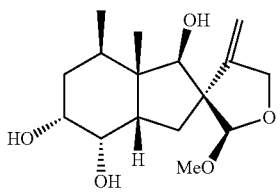

in a chemoselective manner.

5. The process according to claim 4, wherein the metal hydroxide used is selected from the group consisting of KOH, NaOH, Ca(OH)$_2$ and mixtures thereof.

6. The process according to claim 4, wherein selective reduction is carried out in presence of NaBH$_4$, LiBH$_4$, Zn(BH$_4$)$_2$ or AlH$_3$.

7. The process according to claim 4, wherein the organic solvent used is selected from the group consisting of THF, DCM, acetonitrile, DMF, ethyl acetate, DMSO and mixtures thereof.

8. A pharmaceutical composition comprising a compound having formula 1 according to claim 1, a stereoisomer or a pharmaceutically acceptable salt thereof, together with one or more pharmaceutically acceptable excipients and/or vehicles, for inhibiting cellular adhesion.

9. A method of inhibiting cellular adhesion in a human subject having cancer, inflammation or bacterial infection, comprising administering a compound having formula I, according to claim 1, optionally along with a pharmaceutically acceptable excipient and/or vehicle, effective to inhibit cellular adhesion resulting from the cancer, inflammation or bacterial infection in the subject.

10. A method for inhibiting cell adhesion in a subject, wherein the subject is human, comprising administering to the human an effective amount of a compound having formula 1, according to claim 1.

* * * * *